United States Patent

Kai et al.

[11] 4,258,184
[45] Mar. 24, 1981

[54] CEPHALOSPORIN DERIVATIVES

[75] Inventors: Fumio Kai, Fujisawa; Takashi Tsuruoka, Kawasaki; Osamu Makabe, Tokyo; Shigeharu Inouye, Okohama; Hitoshi Ikeda, Kawasaki; Yuzo Kazuno, Hachiohji; Shokichi Nakajima, Yokohama; Shigeo Seki, Tokyo; Taro Niida, Yokohama, all of Japan

[73] Assignee: Meiji Seika Kaisha Ltd., Tokyo, Japan

[21] Appl. No.: 20,224

[22] Filed: Mar. 13, 1979

Related U.S. Application Data

[63] Continuation-in-part of Ser. No. 837,991, Sep. 29, 1977, abandoned.

[30] Foreign Application Priority Data

Oct. 2, 1976 [JP] Japan .................. 51/118727
Mar. 13, 1978 [JP] Japan .................. 53/27784

[51] Int. Cl.³ .................. C07D 501/56
[52] U.S. Cl. .................. 544/27; 544/28
[58] Field of Search .................. 544/27, 28; 424/246

[56] References Cited

U.S. PATENT DOCUMENTS

| 3,948,903 | 4/1976 | Doub et al. | 424/246 |
| 4,053,470 | 10/1977 | Doub et al. | 424/246 |
| 4,154,831 | 5/1979 | Kocsis et al. | 424/246 |

Primary Examiner—Paul M. Coughlan, Jr.

Attorney, Agent, or Firm—Frishauf, Holtz, Goodman & Woodward

[57] ABSTRACT

Novel cephalosporin derivatives having formulae (V) and (III):

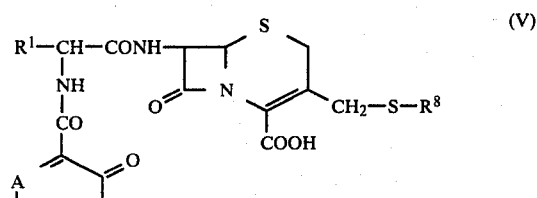

and

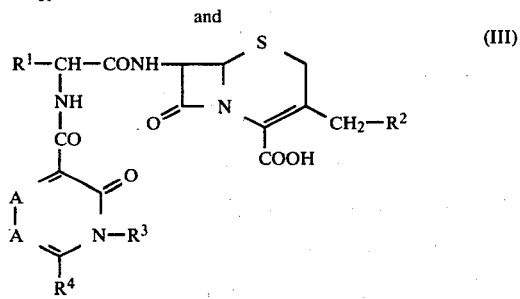

wherein $R^1$, $R^2$, $R^3$, $R^4$, $R^8$ and A are defined as in the specification.

5 Claims, No Drawings

CEPHALOSPORIN DERIVATIVES

BACKGROUND OF THE APPLICATION

This application is a continuation-in-part of application Ser. No. 837,991, filed Sept. 29, 1977, now abandoned.

This invention relates to a process for preparing cephalosporin derivatives or pharmaceutically acceptable salts thereof. Particularly, this invention relates to a process for preparing cephalosporin derivatives having formulae (V) and (III) or pharmaceutically acceptable salts thereof. Further, this invention relates to intermediates of them and a process for preparing the same.

The compounds (V) and (III) are represented by the following formulae:

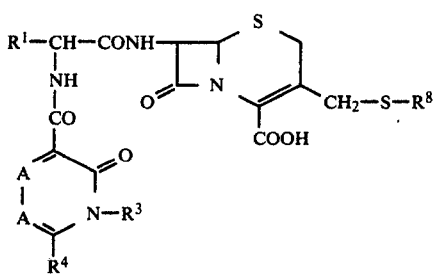

wherein $R^1$ represents an aryl, an alkyl, a cycloalkyl, a cycloalkenyl, a cycloalkadienyl, a furyl or thienyl group, each of which may be substituted; $R^3$ represents hydrogen, a lower alkyl or an aryl group which may be substituted; $R^4$ represents hydrogen, hydroxyl, an alkyl, an aryl which may be substituted, halogen, an amino, a carboxyalkylamino, an alkoxycarbonylalkylamino, a dialkylaminoalkylamino, a mercaptoalkylamino, an alkylthioalkylamino, a hydroxyalkylamino, an alkoxyalkylamino, a bis(hydroxyalkyl)amino, a bis(alkoxyalkyl)amino, an alkoxyalkoxyalkylamino, a hydroxyalkoxyalkylamino, a dialkylamino, a piperidino, a pyrrolidino, a morpholino, a piperazino, N-alkylpiperazino, an arylsulfonamido, an arylcarbonamido, an alkanesulfonamido, an alkanecarbonamido, an alkylthio, a carboxyalkylthio, an alkoxycarbonylalkylthio, a dialkylaminoalkylthio, a hydroxyalkylthio, an alkoxyalkylthio, an alkanesulfinyl, an alkanesulfonyl, a hydrazino, an arylhydrazino, an alkylhydrazino and a

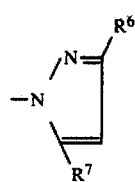

group wherein $R^6$ represents hydrogen or a lower alkyl group, and $R^7$ represents hydrogen, hydroxyl or an alkoxyl group; A represents nitrogen or a

group wherein $R^5$ represents hydrogen, a halogen, a hydroxyl, alkoxyl or an alkyl group; $R^8$ represents a

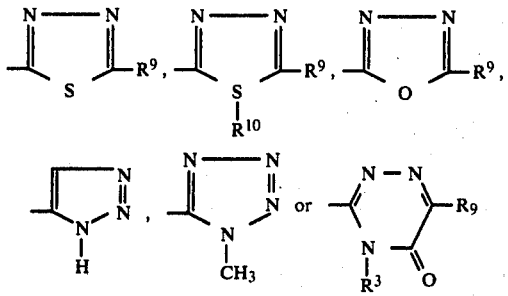

wherein $R^9$ represents hydrogen, a lower alkyl, an aminoalkyl, an aminoaralkyl, 5-alkylmercapto-1,2,4-triazol-3-yl, 5-alkylmercapto-1,3,4-thiadiazol-2-yl, 5-alkylmercapto-1,3,4-oxadiazol-2-yl, 1,2,4-triazol-3-yl, 1,3,4-thiadiazol-2-yl, 1,3,4-oxadiazol-2-yl, an alkylamino, a cycloalkylaminocycloalkyl, a phenyl which may be substituted and a $—(CH_2)_n—COR^{11}$ group wherein $R^{11}$ represents hydroxyl, an alkoxyl and a

group wherein $R^{12}$ and $R^{13}$ which may be the same or different, each represents hydrogen, an alkyl, hydroxyl, amino, an alkylamino, anilino, and an aryl which may be substituted, a hydroxyalkyl, an alkoxyalkyl, an alkoxyalkoxyalkyl, an alkoxyalkoxyalkoxyalkyl, a hydroxyalkoxyalkyl, a hydroxyalkoxyalkoxyalkyl, an alkylthioalkyl, an arylthioalkyl, an alkylaminoalkyl, a dialkylaminoalkyl, a dialkylaminoalkoxyalkyl, a carboxyalkyl, a cycloalkyl, an adamantyl,

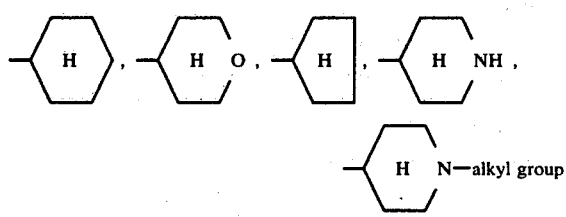

and n represents zero or an inteter of 1 to 4 and $R^3$ is defined as above and $R^{10}$ represents hydrogen, a lower alkyl, amino or an aryl group which may be substituted.

Formula (III):

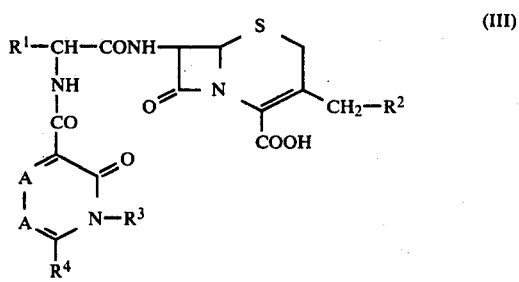

wherein $R^2$ represents hydrogen or a lower alkanoyloxy group and $R^1$, $R^3$, $R^4$ and A have the same meanings as above.

The preparation of the compounds according to this invention will be explained as follows: on the first synthesis, the reaction of a compound having formula (I):

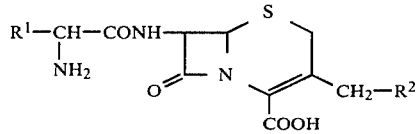
(I)

wherein $R^1$ and $R^2$ are defined as above with a compound having formula (II):

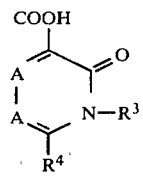
(II)

wherein $R^3$, $R^4$ and A are defined as above or a reactive derivative of the carboxyl group thereof is carried out to form CONH bond by dehydration-condensation of the carboxyl and amino group. This reaction is conventional ones which are applicable for polypeptide synthesis, or for an acylation of 6-amino and 7-amino position in penicillins and cephalosporins. The reactive derivatives are, for example, acid halides such as acid chlorides, mixed acid anhydrides such as various kinds of organic acid (e.g. carbonic acid) and inorganic acid (e.g. sulfuric acid, phosphoric acid), active esters, active thioesters having an electron-attracting alcohol or phenol residual group, active amides and so-called pseudohalogenides such as acid azides and sulfonals. Various kinds of dehydration-condensing agents used for this invention which are applicable for peptide bond formation so as to form a reactive derivative of the carboxyl group and an activated amino derivative, as intermediates, are conventional dehydration-condensing agents used in this art such as carbodiimides, inamines, alcoxyacetylenes, Woodward's reagents, phosphoamides, phosphoric acid cyanide agents, phosphorous acid esters, pyrophosphoric acid esters, phosphorous acid ester halides and phosphorous acid halides. These compounds are used for an acylation of the carboxylic acid and the amino compound in the presence or absence of a base. This peptide formation reaction is carried out using solvents such as water, organic solvents which may contain or do not contain water and non-protonic organic solvents. The reaction temperature is at a range of −50° to 100° C. and the reaction time is usually from dozens of minutes to about six hours. But the reaction conditions are not limited to this scope and other conditions can be optionally selected dependent on kinds of reacting agents, activities of the reagents, scales of the reaction and kinds of solvent. After reaction, the resultant compound can be separated and collected by usual methods. The compounds having formula (III) obtained by the above peptide bond formation reaction:

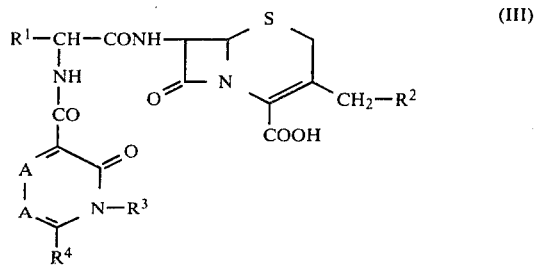
(III)

are valuable compounds as medicals. But, of the compounds (III), in cases where $R^2$ is an alkanoyloxy radical, the alkanoyloxy radical is apt to be hydrolyzed in vivo or in contact with microorganisms and to be changed into antibiotic compounds with lower activity.

For this reason, this alkanoyloxy radical of formula (III) can be substituted with a heterocyclic thio group by the following reaction in order that the decomposition against the esterase can be stabilized and the antibiotic activity can be increased. That is, the compound having formula (III) in which $R^2$ is an alkanoyloxy radical is reacted with a heterocyclic thiol compound having formula (IV):

$$HS-R^8 \qquad (IV)$$

wherein $R^8$ has the same meaning as above to obtain a compound having formula (V):

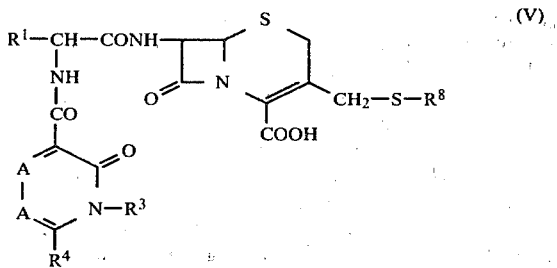
(V)

wherein $R^1$, $R^3$, $R^4$, $R^8$ and A have the same meanings as above.

Such a substitution reaction of the acetoxy group connected in an aryl position with a thiol compound is a conventional one in the art of cephalosporins. The reaction conditions are as follows: the thiol compound may usually be used in an amount of one to 1.5 moles per one mole of the compound (III) to be substituted; The reaction can usually be carried out in a medium such as water or water-containing organic medium at a pH of 5 to about 7 at a temperature of room temperature to 80° C. and finished for several hours to dozens of hours. For the regulation of pH inorganic salts such as potassium hydroxide, potassium carbonate, potassium hydrogen carbonate and potassium phosphate can usually be used. After reaction, the resultant compound can be separated as a free acid or a salt. In the above reaction of the peptide formation and the substitution of the alkanoyloxy group with the heterocyclic thiol compound, the functional group such as hydroxy, mercapto and amino group in the compound having formula (II) is preferred to be adequately protected by a conventional protection method and to be removed after reaction, if desired.

As the second synthesis course, a compound having formula (VI):

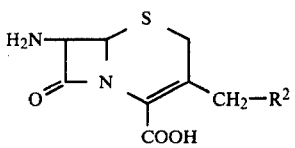

wherein $R^2$ has the same meaning as above is reacted with a compound having formula (VII):

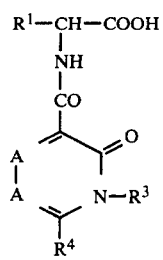

wherein $R^1$, $R^3$, $R^4$ and A have the same meanings as above or a reactive derivative of the carboxyl group in (VII) to give the compound having formula (III). In cases where $R^2$ in formula (III) is an alkanoyloxy group, the compound (III) may be reacted with a heterocyclic thiol compound having formula (V), if desired. The last substitution with the heterocyclic thiol can be carried out under the same conditions as described above.

As the third synthesis course, a compound having formula (I):

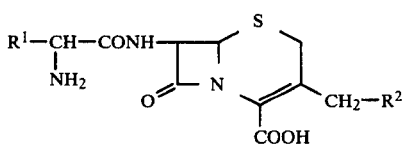

wherein $R^1$ and $R^2$ have the same meanings as above or a compound having formula (X):

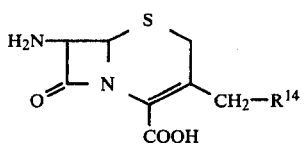

wherein $R^{14}$ represents an alkanoyloxy group is reacted with a compound having formula (IV):

wherein $R^8$ has the same meaning as above for the substitution with the heterocyclic thiol to obtain respectively a compound having formula (IX):

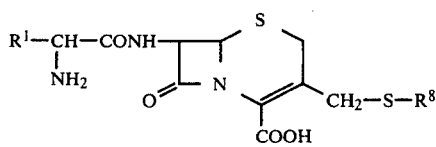

wherein $R^1$ and $R^8$ have the same meanings as above or a compound having formula (XI):

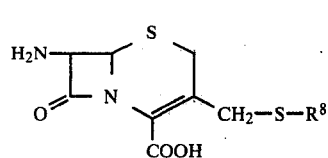

wherein $R^8$ has the same meaning as above. Next, the compound having formula (IX) is reacted with a compound having formula (II) or a reactive derivative of the carboxyl group in (II) to make peptide formation, thus obtaining the desired compound (V). Further, the intermediate compound having formula (XI) is reacted with (a) a compound having formula (VII) or a reactive derivative of its carboxyl group, or (b) a compound having formula (XII):

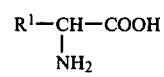

wherein $R^1$ has the same meaning as above or a reactive derivative of its carboxyl group to obtain a compound having formula (IX), which is then reacted with a compound having formula (II) or a reactive derivative of its carboxyl group to give the desired compound (V). This compound can also be obtained from the compound (IX) by means of (a) or (b) method. In the above peptide bond formation reaction and substitution reaction of the alkanoyloxy group with a heterocyclic thiol group, in cases where the compound having formulae (I), (II), (III), (VI), (VII), (VIII), (IX), (X), (XI) and (XII) have functional groups described above, the functional groups are preferred to be protected adequately, if desired. As to protecting groups for amino group, the protection using protecting groups such as t-butoxycarbonyl, enamine type and silazane type are preferred. As to protecting groups for the carboxyl group, protecting groups such as ester groups, e.g. alkyl esters, trichloroethyl ester, p-nitrophenyl ester, p-nitrobenzyl ester, alkanoyloxymethyl ester, e.g. pivaloyloxymethyl ester, and acetoxymethyl ester, benzhydryl ester, trityl ester, p-methoxybenzyl ester and silyl esters are preferred. These groups are not meant to be limited. The reaction resultant having protecting group can be submitted to the protecting group removing reaction under mild conditions, if necessary, or used to subsequent reactions as starting materials as they are without removing the protecting group, if desired.

The compound having formulae (V) and (III) can also easily be transformed into pharmaceutically acceptable salts such as sodium salt, potassium salt and several amine salts.

The typical compounds having formula (V) according to this invention are mainly devided into the compounds of two groups having formulae (Va) and (Vb) as follows:

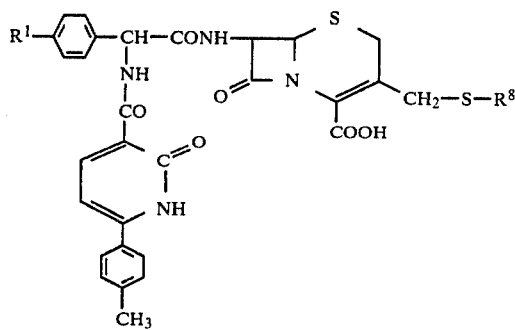

wherein

1. $R^1 = H$, $R^8 = $ thiadiazolyl,
2. $R^1 = H$, $R^8 = $ thiadiazolyl-$CONH_2$,
3. $R^1 = H$, $R^8 = $ thiadiazolyl-$CON(CH_3)_2$,
4. $R^1 = H$, $R^8 = $ thiadiazolyl-$CONHCH_3$,
5. $R^1 = H$, $R^8 = $ thiadiazolyl-$CON(C_2H_5)_2$,
6. $R^1 = H$, $R^8 = $ thiadiazolyl-$CONHC_2H_5$,
7. $R^1 = H$, $R^8 = $ thiadiazolyl-$CONHCH_2CH_2NH_2$,
8. $R^1 = H$, $R^8 = $ thiadiazolyl-$CONHCH_2CH_2N(C_2H_5)_2$,
9. $R^1 = H$, $R^8 = $ thiadiazolyl-$CONHCH_2CH_2CH_2NH_2$,
10. $R^1 = H$, $R^8 = $ thiadiazolyl-$CONHCH_2CH_2CH_2N(C_2H_5)_2$,
11. $R^1 = H$, $R^8 = $ thiadiazolyl-$CONHCH_2CH_2N(CH_3)_2$,
12. $R^1 = H$, $R^8 = $ thiadiazolyl-$CONHCH_2CH_2CH_2N(CH_3)_2$,
13. $R^1 = H$, $R^8 = $ thiadiazolyl-$CONHCH(CH_3)_2$,
14. $R^1 = H$, $R^8 = $ thiadiazolyl-$CON$-piperidinyl,
15. $R^1 = H$, $R^8 = $ thiadiazolyl-$CON$-morpholinyl,
16. $R^1 = H$, $R^8 = $ thiadiazolyl-$CON$-piperazinyl-NH,
17. $R^1 = H$, $R^8 = $ thiadiazolyl-$CON$-piperazinyl-$N-CH_3$,
18. $R^1 = H$, $R^8 = $ thiadiazolyl-$CON$-piperazinyl-$N-C_2H_5$,
19. $R^1 = H$, $R^8 = $ thiadiazolyl-$CON$-pyrrolidinyl,
20. $R^1 = H$, $R^8 = $ thiadiazolyl-$CONHNH_2$,
21. $R^1 = H$, $R^8 = $ thiadiazolyl-$CONHCH_2CH=CH_2$,
22. $R^1 = H$, $R^8 = $ thiadiazolyl-$CONHCH_2CH_2CH_3$,
23. $R^1 = H$, $R^8 = $ thiadiazolyl-$CONHCH_2CH_2OCH_2CH_2OH$,
24. $R^1 = H$, $R^8 = $ thiadiazolyl-$CONHCH_2CH_2CH_2OCH_3$,
25. $R^1 = H$, $R^8 = $ thiadiazolyl-$CONHC(=NH)NH_2$,
26. $R^1 = H$, $R^8 = $ thiadiazolyl-$CONHCH_2CH_2OH$,
27. $R^1 = H$, $R^8 = $ thiadiazolyl-$CONHOH$,
28. $R^1 = H$, $R^8 = $ thiadiazolyl-$CON(CH_3)OH$,
29. $R^1 = H$, $R^8 = $ bis-thiadiazolyl-S-,
30. $R^1 = H$, $R^8 = $ thiadiazolyl-$COOH$,
31. $R^1 = H$, $R^8 = $ thiadiazolyl-$COOC_2H_5$,
32. $R^1 = H$, $R^8 = $ thiadiazolyl-$CON(CH_2CH_2OH)_2$, -continued 33. $R^1 = H$, $R^8 =$ [thiadiazole]-CH₂COOH, 34. $R^1 = H$, $R^8 =$ [N-methyl triazole]-CH₂COOH, 35. $R^1 = H$, $R^8 =$ [NH-triazole]-CH₂CH₂COOH, 36. $R^1 = H$, $R^8 =$ [N-methyl triazole]-CH₂CH₂COOH, 37. $R^1 = H$, $R^8 =$ [N-methyl triazole], 38. $R^1 = H$, $R^8 =$ [N-methyl tetrazole], 39. $R^1 = H$, $R^8 =$ [thiadiazole]-CH₃, 40. $R^1 = H$, $R^8 =$ [HN-triazole], 41. $R^1 = H$, $R^8 =$ [thiadiazole]-CONHCH₂CH₂COOH, 42. $R^1 = OH$, $R^8 =$ [thiadiazole]-CONHCH₂CH₂NH₂, 43. $R^1 = OH$, $R^8 =$ [thiadiazole]-CONHCH₂CH₂N(C₂H₅)₂, 44. $R^1 = OH$, $R^8 =$ [thiadiazole]-CONHCH₂CH₂CH₂NH₂, 45. $R^1 = OH$, $R^8 =$ [thiadiazole]-CONHCH₂CH₂CH₂N(C₂H₅)₂, 46. $R^1 = OH$, $R^8 =$ [thiadiazole]-CONHCH₂CH₂N(CH₃)₂, 47. $R^1 = OH$, $R^8 =$ [thiadiazole]-CONHCH₂CH₂CH₂N(CH₃)₂, 48. $R^1 = OH$, $R^8 =$ [thiadiazole]-CON(C₆H₅)—CH₂CH₂N(C₂H₅)₂, 49. $R^1 = OH$, $R^8 =$ [thiadiazole]-CON[piperazine]NH, 50. $R^1 = OH$, $R^8 =$ [thiadiazole]-CON[piperazine]N—C₂H₅, 51. $R^1 = OH$, $R^8 =$ [thiadiazole]-CON[piperazine]N—CH₃, 52. $R^1 = OH$, $R^8 =$ [thiadiazole], 53. $R^1 = OH$, $R^8 =$ [thiadiazole]-[thiadiazole], 54. $R^1 = OH$, $R^8 =$ [thiadiazole]-CONH₂, 55. $R^1 = OH$, $R^8 =$ [thiadiazole]-CON(CH₃)₂, 56. $R^1 = OH$, $R^8 =$ [thiadiazole]-CONHCH₃, 57. $R^1 = OH$, $R^8 =$ [thiadiazole]-CON(C₂H₅)₂, 58. $R^1 = OH$, $R^8 =$ [thiadiazole]-CONHC₂H₅, 59. $R^1 = OH$, $R^8 =$ [thiadiazole]-CONHCH(CH₃)₂, 60. $R^1 = OH$, $R^8 =$ [thiadiazole]-CON[piperidine], 61. $R^1 = OH$, $R^8 =$ [thiadiazole]-CON[pyrrolidine], 62. $R^1 = OH$, $R^8 =$ [thiadiazole]-CON[morpholine]O, 63. $R^1 = OH$, $R^8 =$ [thiadiazole]-CONHNH₂, 64. $R^1 = OH$, $R^8 =$ [thiadiazole]-CONHCH₂CH=CH₂, 65. $R^1 = OH$, $R^8 =$ [thiadiazole]-CONHCH₂CH₂CH₃, 66. $R^1 = OH$, $R^8 =$ [thiadiazole]-CONHCH₂CH₂CH₂CH₃, -continued 67. R¹ = OH, R⁸ = [thiadiazole]-CONHCH₂CH₂OCH₂CH₂OH, 68. R¹ = OH, R⁸ = [thiadiazole]-CONHCH₂CH₂CH₂OCH₃, 69. R¹ = OH, R⁸ = [thiadiazole]-CONHCNH₂
                                    ‖
                                    NH 70. R¹ = OH, R⁸ = [thiadiazole]-CONHCH₂CH₂OH, 71. R¹ = OH, R⁸ = [thiadiazole]-CON—CH₂CH₂OH,
                                 |
                                 CH₃

72. R¹ = OH, R⁸ = [thiadiazole]-CON(CH₂CH₂OH)₂,

73. R¹ = OH, R⁸ = [thiadiazole]-CONHOH,

74. R¹ = OH, R⁸ = [thiadiazole]-CON—OH,
                                 |
                                 CH₃

75. R¹ = OH, R⁸ = [thiadiazole]-COOH,

76. R¹ = OH, R⁸ = [thiadiazole]-COOC₂H₅,

77. R¹ = OH, R⁸ = [1H-triazole]-CH₂COOH,

78. R¹ = OH, R⁸ = [N-CH₃-triazole]-CH₂COOH,

79. R¹ = OH, R⁸ = [1H-triazole]-CH₂CH₂COOH,

80. R¹ = OH, R⁸ = [N-CH₃-triazole]-CH₂CH₂COOH,

81. R¹ = OH, R⁸ = [tetrazole N-CH₃],

82. R¹ = OH, R⁸ = [N-CH₃-triazole],

83. R¹ = OH, R⁸ = [thiadiazole]-CH₃,

84. R¹ = OH, R⁸ = [1H-tetrazole],

85. R¹ = OH, R⁸ = [thiadiazole]-CONHCH₂CH₂COOH,

86. R¹ = OH, R⁸ = [1H-triazole]-CH₂NH₂,

87. R¹ = OH, R⁸ = [1H-triazole]-CHCH₃,
                                |
                                NH₂

88. R¹ = OH, R⁸ = [1H-triazole]-CHCH₂CH(CH₃)₂,
                                |
                                NH₂

89. R¹ = OH, R⁸ = [1H-triazole]-CH—CH₂—C₆H₅,
                                |
                                NH₂

90. R¹ = OH, R⁸ = [N-CH₃-triazole]-CHCH₃,
                                   |
                                   NH₂

91. R¹ = OH, R⁸ = [N-CH₃-triazole]-CHCH₂CH(CH₃)₂,
                                   |
                                   NH₂

92. R¹ = OH, R⁸ = [N-phenyl-triazole]-CH₂NH₂,

93. R¹ = OH, R⁸ = [1H-triazole]-CH₂NH₂,

94. R¹ = OH, R⁸ = [N-CH₃-triazole]-CHCH₂—C₆H₅,
                                   |
                                   NH₂

95. R¹ = OH, R⁸ = [1H-triazole]-CH—C₆H₄—OH,
                                |
                                NH₂ and

-continued

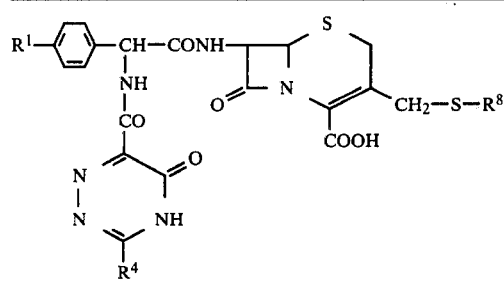
(Vb)

wherein

96. $R^1 = H$, $R^4 = OH$, $R^8 = $ [N—N triazole-S-],

97. $R^1 = H$, $R^4 = OH$, $R^8 = $ [thiadiazole]-CONH$_2$,

98. $R^1 = H$, $R^4 = OH$, $R^8 = $ [thiadiazole]-CONHNH$_2$,

99. $R^1 = H$, $R^4 = OH$, $R^8 = $ [thiadiazole]-CONHCH$_3$,

100. $R^1 = H$, $R^4 = OH$, $R^8 = $ [thiadiazole]-CON(CH$_3$)$_2$,

101. $R^1 = H$, $R^4 = OH$, $R^8 = $ [thiadiazole]-CONHCH$_2$CH$_2$NH$_2$,

102. $R^1 = H$, $R^4 = OH$, $R^8 = $ [thiadiazole]-CONHCH$_2$CH$_2$N(C$_2$H$_5$)$_2$, 103. $R^1 = H$, $R^4 = OH$, $R^8 = $ [thiadiazole]-CON(piperazine)NH, 104. $R^1 = H$, $R^4 = OH$, $R^8 = $ [thiadiazole]-CON(piperazine)N—CH$_3$, 105. $R^1 = H$, $R^4 = OH$, $R^8 = $ [thiadiazole]-CON(C$_2$H$_5$)—CH$_2$CH$_2$N(C$_2$H$_5$)$_2$, 106. $R^1 = OH$, $R^4 = OH$, $R^8 = $ [thiadiazole], 107. $R^1 = OH$, $R^4 = OH$, $R^8 = $ [thiadiazole]-CONH$_2$, 108. $R^1 = OH$, $R^4 = OH$, $R^8 = $ [thiadiazole]-CONHNH$_2$, 109. $R^1 = OH$, $R^4 = OH$, $R^8 = $ [thiadiazole]-CONHCH$_3$, 110. $R^1 = OH$, $R^4 = OH$, $R^8 = $ [thiadiazole]-CON(CH$_3$)$_2$, 111. $R^1 = OH$, $R^4 = OH$, $R^8 = $ [thiadiazole]-CONHCH$_2$CH$_2$NH$_2$, 112. $R^1 = OH$, $R^4 = OH$, $R^8 = $ [thiadiazole]-CONHCH$_2$CH$_2$N(C$_2$H$_5$)$_2$, 113. $R^1 = OH$, $R^4 = OH$, $R^8 = $ [thiadiazole]-CON(piperazine)NH, 114. $R^1 = OH$, $R^4 = OH$, $R^8 = $ [thiadiazole]-CON(piperazine)N—CH$_3$, 115. $R^1 = OH$, $R^4 = OH$, $R^8 = $ [thiadiazole]-CON—CH$_2$CH$_2$N(C$_2$H$_5$)$_2$, with C$_5$H$_5$ 116. $R^1 = OH$, $R^4 = SCH_3$, $R^8 = $ [thiadiazole], 117. $R^1 = OH$, $R^4 = SCH_3$, $R^8 = $ [thiadiazole]-CONH$_2$, 118. $R^1 = OH$, $R^4 = SCH_3$, $R^8 = $ [thiadiazole]-CONHNH$_2$, 119. $R^1 = OH$, $R^4 = SCH_3$, $R^8 = $ [thiadiazole]-CONHCH$_3$, 120. $R^1 = OH$, $R^4 = SCH_3$, $R^8 = $ [thiadiazole]-CON(CH$_3$)$_2$, 121. $R^1 = OH$, $R^4 = SCH_3$, $R^8 = $ [thiadiazole]-CONHCH$_2$CH$_2$NH$_2$, 122. $R^1 = OH$, $R^4 = SCH_3$, $R^8 = $ [thiadiazole]-CONHCH$_2$CH$_2$N(C$_2$H$_5$)$_2$, 123. $R^1 = OH$, $R^4 = SCH_3$, $R^8 = $ [thiadiazole]-CONHCH$_2$CH$_2$CH$_3$N(CH$_3$)$_2$, 124. $R^1 = OH$, $R^4 = SCH_3$, $R^8 = $ [thiadiazole]-CON(piperazine)NH, 125. $R^1 = OH$, $R^4 = SCH_3$, $R^8 = $ [thiadiazole]-CON(piperazine)N—CH$_3$,

126. $R^1 = OH$, $R^4 = SCH_3$,

126. $R^8 = $ [thiadiazolyl]-CONCH$_2$CH$_2$N(C$_2$H$_5$)$_2$,
   |
   C$_2$H$_5$ 127. $R^1 = H$, $R^4 = $ -N(pyrazolyl) or 1-pyrazolyl, $R^8 = $ [thiadiazolyl], 128. $R^1 = H$, $R^4 = $ 1-pyrazolyl, $R^8 = $ [thiadiazolyl]-CONH$_2$, 129. $R^1 = H$, $R^4 = $ 1-pyrazolyl, $R^8 = $ [thiadiazolyl]-CONHNH$_2$, 130. $R^1 = H$, $R^4 = $ 1-pyrazolyl, $R^8 = $ [thiadiazolyl]-CONHCH$_3$, 131. $R^1 = H$, $R^4 = $ 1-pyrazolyl, $R^8 = $ [thiadiazolyl]-CON(CH$_3$)$_2$, 132. $R^1 = H$, $R^4 = $ 1-pyrazolyl,
   $R^8 = $ [thiadiazolyl]-CONHCH$_2$CH$_2$NH$_2$, 133. $R^1 = H$, $R^4 = $ 1-pyrazolyl,
   $R^8 = $ [thiadiazolyl]-CONHCH$_2$CH$_2$N(C$_2$H$_5$)$_2$, 134. $R^1 = H$, $R^4 = $ 1-pyrazolyl,
   $R^8 = $ [thiadiazolyl]-CON(piperazinyl)NH, 135. $R^1 = H$, $R^4 = $ 1-pyrazolyl,
   $R^8 = $ [thiadiazolyl]-CON(piperazinyl)N—CH$_3$, 136. $R^1 = H$, $R^4 = $ 1-pyrazolyl,
   $R^8 = $ [thiadiazolyl]-CON—CH$_2$CH$_2$N(C$_2$H$_5$)$_2$,
   |
   C$_2$H$_5$ 137. $R^1 = OH$, $R^4 = $ 1-pyrazolyl,
   $R^8 = $ [thiadiazolyl], 138. $R^1 = OH$, $R^4 = $ 1-pyrazolyl, $R^8 = $ [thiadiazolyl]-CONH$_2$, 139. $R^1 = OH$, $R^4 = $ 1-pyrazolyl,
   $R^8 = $ [thiadiazolyl]-CONHCH$_3$, 140. $R^1 = OH$, $R^4 = $ 1-pyrazolyl,
   $R^8 = $ [thiadiazolyl]-CON(CH$_3$)$_2$, 141. $R^1 = OH$, $R^4 = $ 1-pyrazolyl,
   $R^8 = $ [thiadiazolyl]-CONHNH$_2$, 142. $R^1 = OH$, $R^4 = $ 1-pyrazolyl,
   $R^8 = $ [thiadiazolyl]-CONHCH$_2$CH$_2$NH$_2$, 143. $R^1 = OH$, $R^4 = $ 1-pyrazolyl,
   $R^8 = $ [thiadiazolyl]-CONHCH$_2$CH$_2$N(C$_2$H$_5$)$_2$, 144. $R^1 = OH$, $R^4 = $ 1-pyrazolyl,
   $R^8 = $ [thiadiazolyl]-CON(piperazinyl)NH, 145. $R^1 = OH$, $R^4 = $ 1-pyrazolyl,
   $R^8 = $ [thiadiazolyl]-CON(piperazinyl)N—CH$_3$, 146. $R^1 = OH$, $R^4 = $ 1-pyrazolyl,
   $R^8 = $ [thiadiazolyl]-CON(piperazinyl)N—C$_2$H$_5$ and 147. $R^1 = OH$, $R^4 = $ 1-pyrazolyl,
   $R^8 = $ [thiadiazolyl]-CON—CH$_2$CH$_2$N(C$_2$H$_5$)$_2$
   |
   C$_2$H$_5$ The representative compounds having formula (III) are as follows:
1. 7-{D-(—)-α-[2-hydroxy-6-(p-tolyl)pyridine-3-carbonylamino]-phenylacetamido}-3-acetoxymethyl-3-cephem-4-carboxylic acid
2. 7-{D-(—)-α-[2-hydroxy-6-(p-tolyl)pyridine-3-carbonylamino]-p-hydroxyphenylacetamido}-3-acetoxymethyl-3-cephem-4-carboxylic acid
3. 7-{D-(—)-α-(5-hydroxy-3-methylthio-asymmetrical-triazine-6-carbonylamino)-p-hydroxyphenylacetamido}-3-acetoxymethyl-3-cephem-4-carboxylic acid
4. 7-{D-(—)-α-(5-hydroxy-3-methylthio-asymmetrical-triazine-6-carbonylamino)-phenylacetamido}-3-acetoxymethyl-3-cephem-4-carboxylic acid
5. 7-{D-(—)-α-(3,5-dihydroxy-asymmetrical-triazine-6-carbonylamino)-p-hydroxyphenylacetamido}-3-acetoxymethyl-3-cephem-4-carboxylic acid
6. 7-{D-(—)-α-(3,5-dihydroxy-asymmetrical-triazine-6-carbonylamino)phenylacetamido}-3-acetoxymethyl-3-cephem-4-carboxylic acid
7. 7-{D-(—)-α-[5-hydroxy-3-(1-pyrazolyl)-asymmetrical-triazine-6-carbonylamino]phenylacetamido}-3-acetoxymethyl-3-cephem-4-carboxylic acid and
8. 7-{D-(—)-α-[5-hydroxy-3-(1-pyrazolyl)-asymmetrical-triazine-6-carbonylamino]-p-hydroxyphenylacetamido}-3-acetoxymethyl-3-cephem-4-carboxylic acid The object compounds according to this invention are novel ones and have broad and strong antibiotic activity for gram positive and negative organisms and further efficient activity for gram negative resistant organisms including Pseudomonas aeruginosa for which known cephalosporin derivatives have not been effective. Therefore, these compounds are promising antibiotics. Comparative tests of some compounds according to this invention with carbenicillin disodium are shown in Table 1.

These compounds are administered orally or parenterally, for example, in the shape of capsules, tablets or injections. Injection is generally preferred. The dosage varies with ages, symptoms and weights but about 250 mg of 3000 mg a day can be divisionally administered for an adult in three to four times. But more than the dosage amount described above can be used under necessary conditions.

The toxicity of the compounds according to this invention is excellently low. For example, when the compound obtained by Example 2 was administered peritoneally, among 6 mice administered any mouse did not die even in a dosage amount of 200 mg/1 kg. As is clear from above, the compounds according to this invention are not only low in toxicity and excellent in anti-biotic activity but also have a prolonged action after administration. Therefore, they show excellent infection cure effect and infection-defense effect in before-or after-administration and in less dosage in comparison with known cephalosporin derivatives, for example, cephalothin, cefazolin or cephaloridine.

This invention will be explained in detail by the following examples.

TABLE 1

| Organisms used | Minimum prohibiting concentration (γ/ml) by means of agar plate dilution method | | | |
|---|---|---|---|---|
| | The compound of Example 2 | The compound of Example 8 | Carbenicillin disodium | Cefazolin Na |
| Staphylococcus aureus 209p JC-1 | 0.78 | 0.20 | 0.39 | 0.10 |
| Staphylococcus aureus Smith S-424 | 0.78 | 0.39 | 0.39 | 0.78 |
| Staphylococcus aureus No. 26 | 6.25 | 3.13 | 25 | 3.13 |
| Bacillus subtilis ATCC 6633 | 1.56 | 0.78 | 0.39 | 0.20 |
| Escherichia coli NIHJ JC-2 | 25 | 12.5 | 12.5 | 6.25 |
| Escherichia coli K-12 IAM 1264 | 6.25 | 1.56 | 12.5 | 3.13 |
| Escherichia coli C73-1 | 25 | 6.25 | 25 | 6.25 |
| Salmonella typhi O-901-W | 3.13 | 1.56 | 12.5 | 3.13 |
| Salmonella enteriditis No. 11 | 0.39 | 0.78 | 50 | 3.13 |
| Proteus morganii Kono | 100 | 25 | 12.5 | >100 |
| Proteus species C73-25 | 25 | 50 | 50 | 3.13 |
| Proteus species C73-34 | 12.5 | 12.5 | 50 | 12.5 |
| Enterobacter species C73-17 | 50 | 12.5 | >100 | 50 |
| Serratia species No. 2 | 100 | 50 | 50 | >100 |
| Serratia species MS-2 | 50 | 50 | 12.5 | >100 |
| Pseudomonas aeruginosa IAM 1007 | 100 | 100 | >100 | >100 |
| Pseudomonas species C73-2 | 100 | 50 | >100 | >100 |
| Pseudomonas species C73-83 | 100 | 100 | >100 | >100 |
| Vibrio parahaemolyticus K-5 | 25 | 3.13 | >100 | 6.25 |
| Vibrio parahaemolyticus K-7 | 12.5 | 3.13 | 50 | 12.5 |

TABLE 2

| organisms used | Minimum inhibition concentration (γ/ml) by means of agar plate dilution method | | |
|---|---|---|---|
| | Compound in Example 56 | Compound in Example 57 | Carbenicillin disodium |
| Staphylococcus aureus Smith S-424 | 1.56 | 12.5 | 0.39 |
| Staphylococcus aureus Smith No. 26 | 6.25 | 50 | 25 |
| Salmonella typhi O-901-W | 1.56 | 6.25 | 12.5 |
| Salmonella enteritidis N0. 11 | 1.56 | 3.13 | 50 |
| Klebsiella pneumoniae | 25 | 50 | 25 |
| Proteus morganii Kono | 12.5 | 100 | 12.5 |
| Vibrio parahaemolyticus K-5 | 25 | 25 | >100 |

TABLE 2-continued

| organisms used | Minimum inhibition concentration (γ/ml) by means of agar plate dilution method | | |
|---|---|---|---|
| | Compound in Example 56 | Compound in Example 57 | Carbenicillin disodium |

EXAMPLE 1

To a suspension of 1.1 g of 7-(D(—)-α-aminophenylacetamido)-3-acetoxymethyl-3-cephem-4-carboxylic acid in 10 ml of dichloromethane were added 550 mg of triethylamine, 1 g of dimethylformamide and 1 g of p-nitrophenyl 2-hydroxy-6-(p-tolyl)-pyridine-3-carboxylate in order and the mixture was stirred at room temperature for 1.5 hours. The solvent was evaporated in vacuo and to the residue were added 20 ml of water and 10 ml of 1N hydrochloric acid to give crystals, which were filtered out and washed with water and ether. These crystals were further dissolved in a combined solution of 6 ml of 0.5N sodium hydrogen carbonate and 15 ml of water and the undissolved substance was filtered and washed with water. To the filtrate combined with the washing water 3 ml of 1N hydrochloric acid was added under stirring to give white crystals, which were filtered, washed with water and dried to give 1.05 g of 7-{D-(—)-α-[2-hydroxy-6-(p-tolyl) pyridine-3-carbonylamino]-phenylacetamido}-3-acetoxymethyl-3-cephem-4-carboxylic acid with m.p. 191° to 194° C. (decomp). IR spectrum (Nujol) cm$^{-1}$: 1780 (β-lactam), 1730, 1665, 1620, (COOH, CONH). NMR spectrum (DMSO-d$_6$-TSP) δ ppm: 2.37(s. 3H, —OCOC$\underline{H}_3$); 2.02(s. 3H, tolyl-C$\underline{H}_3$); 3.47(s. 2H, —C$\underline{H}_2$— at 2-position); 4.84(ABq. 2H, —C$\underline{H}_2$— at 3-position); 5.03(d, 1H, J=5, H at 6-position); 5.83(d.d. 1H, H at 7-position); 5.88(d. 1H, J=7.5,

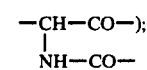

6.75(d. 1H, J=7.7, pyridine ring proton); 8.31(d. 1H, J=7.7, pyridine ring proton); 7.50(ABq. 4H, toluene ring proton); 7.38(s. 5H phenyl ring proton); 9.43(d. J=8, N$\underline{H}$ at 7-position); 10.78(d. J=7.5,

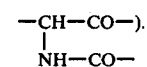

EXAMPLE 2

In 0.714 ml of 0.5N sodium hydrogen carbonate was dissolved 57.5 mg of 5-mercapto-1,3,4-thiadiazol-2-carboxylic acid amide (with m.p. 215° to 218° C. (decomp)) and 200 mg of 7-{D(—)-α-[2-hydroxy-6-(p-tolyl)pyridine-3-carbonylamino]phenylacetamido}-3-acetoxymethyl-3-cephem-4-carboxylic acid and 0.714 ml of 0.5N sodium hydrogen carbonate were added thereto. The mixture was adjusted to pH from 6.4 to 6.6. The mixture was warmed at 64° to 65° C. for 5 hours under nitrogen atmosphere. After the reaction, 10 ml of water was added and the solution filtered while hot. The filtrate was ice-cooled and 1 ml of 1N hydrochloric acid was added thereto under stirring to give pale yellow crystals, which were filtered out, washed with water and dried to give 142 mg of 7-{D(−)-α-[2-hydroxy-6-(p-tolyl)pyridine-3-carbonylamino]phenylacetamido}-3-(5-carbamoyl-1,3,4-thiadiazol-2-ylthiomethyl)-3-cephem-4-carboxylic acid having m.p. 188° to 189° C. (decomp.).

IR spectrum (Nujol) cm$^{-1}$: 1780 (β-lactam), 1730 to 1650, 1610 to 1590 (COOH, CONH).

EXAMPLE 3

In 0.54 ml of 0.5N sodium hydrogen carbonate, 46.7 mg of 2-(N-methylcarbamoyl)-5-mercapto-1,3,4-thiadiazole with m.p. 249° to 250° C. (decomp.) was dissolved and 200 mg of 7-{D(−)-α-[2-hydroxy-6-(p-tolyl)pyridine-3-carboxylamino]phenylacetamido}-3-acetoxymethyl-3-cephem-4-carboxylic acid and 0.535 ml of 0.5N sodium hydrogen carbonate were added thereto. After the mixture being dissolved, the air of the bottle was substituted with nitrogen and the bottle, after tightly closed, was warmed at 65° to 66° C. for 6 hours. After the reaction, 0.7 ml of 1N hydrochloric acid was added to the solution gradually with ice-cooling under stirring to give crystals, which were filtered, washed with water and dried to give 190 mg of 7-{D(−)-α-[2-hydroxy-6-(p-tolyl)pyridine-3-carbonylamino]-phenylacetamido}-3-[5-(N-methylcarbamoyl)-1,3,4-thiadiazol-2-ylthiomethyl]-3-cephem-4-carboxylic acid with m.p. 185° to 189° C. (decomp.).

IR spectrum (Nujol) cm$^{-1}$: 1784 (β-lactam), 1644, 1615 (COOH, CONH).

EXAMPLE 4

In 0.714 ml of 0.5N sodium hydrogen carbonate and 2 ml of water was dissolved 67.5 mg of 2-(N-ethylcarbamoyl)-5-mercapto-1,3,4-thiadiazole with m.p. 176° to 178° C. and 200 mg of 7-{D(−)-α-[2-hydroxy-6-(p-tolyl)pyridine-3-carbonylamino]phenylacetamido}-3-acetoxymethyl-3-cephem-4-carboxylic acid and 0.714 ml of 0.5N sodium hydrogen carbonate were added thereto. The mixture was dissolved and warmed at 64° to 65° C. for six hours under nitrogen atmosphere. After reaction, the solution was cooled with ice and 1 ml of 1N hydrochloric acid was added under stirring to give white crystals, which were filtered and washed with water and dried to give 200 mg of 7-{D(−)-α-[2-hydroxy-6-(p-tolyl)pyridine-3-carbonylamino]-phenylacetamido}-3-[5-N-ethylcarbamoyl)-1,3,4-thiadiazole-2-ylthiomethyl]-3-cephem-4-carboxylic acid with m.p. 175° to 178° C. (decomp.).

IR spectrum (Nujol) cm$^{-1}$: 1878 (β-lactam), 1657, 1613 (COOH, CONH).

EXAMPLE 5

In 2 ml of water was dissolved with heating 73 mg of 2-[N-(2-aminoethyl)carbamoyl]-5-mercapto-1,3,4-thiadiazole with m.p. 248° to 250° C. (decomp.) and 200 mg of 7-{D(−)-α-[2-hydroxy-6-(p-tolyl)pyridine-3-carbonylamino]phenylacetamido}-3-acetoxymethyl-3-cephem-4-carboxylic acid and 0.714 ml of 0.5N sodium hydrogen carbonate was added and dissolved thereto. The solution was warmed at 64° to 65° C. for 6 hours under nitrogen atmosphere. After cooling, crystals that appeared were filtered, washed with water and dried. Thus obtained was 153 mg of 7-{D(−)-α-[2-hydroxy-6-(p-tolyl)pyridine-3-carbonylamino]phenylacetamido}-3-{5-[N-(2-aminoethyl)carbamoyl]-1,3,4-thiadiazol-2-ylthiomethyl}-3-cephem-4-carboxylic acid with m.p. 200° to 205° C. (decomp.).

IR spectrum (Nujol) cm$^{-1}$: 1765 (β-lactam), 1663, 1613 (COOH, CONH)

EXAMPLE 6

In 0.714 ml of 0.5N sodium hydrogen carbonate was dissolved 73 mg of 2-[N-(2-hydroxyethyl)carbamoyl]-5-mercapto-1,3,4-thiadiazole with m.p. 205° to 206° C. (decomp.) and 200 mg of 7-{D(−)-α-[2-hydroxy-6-(p-tolyl)pyridine-3-carbonylamino]phenylacetamido}-3-acetoxymethyl-3-cephem-4-carboxylic acid and 0.714 ml of 0.5N sodium hydrogen carbonate were added and dissolved thereto. This solution was treated in the same way as in Example 2 to give 172 mg of 7-{D(−)-α-[2-hydroxy-6-(p-tolyl)pyridine-3-carbonylamino]-phenylacetamido}-3-{5-[N-(2-hydroxyethyl)carbamoyl]-1,3,4-thiadiazol-2-ylthiomethyl}-3-cephem-4-carboxylic acid with m.p. 188° to 192° C. (decomp.) as white crystals.

IR spectrum (Nujol) cm$^{-1}$: 1779 (β-lactam), 1660, 1614 (COOH, CONH).

EXAMPLE 7

1.68 g of 7-[D(−)-α-amino-p-hydroxyphenylacetamido]-3-acetoxymethyl-3-cephem-4-carboxylic acid was suspended in 25 ml of dichloromethane and then 1.6 g of triethylamine was added thereto. The mixture was stirred with ice-cooling for 30 minutes and 24 ml of dimethylformamide and 1.4 g of p-nitrophenyl 2-hydroxy-6-(p-tolyl)pyridine-3-carboxylate were added thereto. The mixture was stirred with ice-cooling for about 4 hours. After the solvent was evaporated under reduced pressure, 30 ml of water and 15 ml of 1N hydrochloric acid were added to the residue with ice-cooling to give white crystals, which were filtered and washed with water and ether. These crystals were dissolved in 0.5N sodium hydrogen carbonate and the undissolved substance was filtered out. To the filtrate 4 ml of 1N hydrochloric acid was added gradually to give white crystals, which were filtered, washed with water and dried to give 2.6 g of 7-{D(−)-α-[2-hydroxy-6-(p-tolyl)pyridine-3-carbonylamino]-p-hydroxyphenylacetamido}-3-acetoxymethyl-3-cephem-4-carboxylic acid with m.p. 191° to 194° C. (decomp.).

IR spectrum (Nujol) cm$^{-1}$: 1774 (β-lactam), 1772, 1660, 1613 (COOH, CONH).

NMR spectrum (DMSO-d$_6$-TSP) δ (ppm): 2.02(s. 3H, —O—COC$\underline{H}_3$); 2.40(s. 3H, tolyl-C$\underline{H}_3$); 3.47(s. 2H, —C$\underline{H}_2$— at 2-position); 4.88(ABq. 2H, —C$\underline{H}_2$— at 3-position); 5.07(d. 1H, J=5, $\underline{H}$ at 6-position); 5.77(d.d. 1H, H at 7-position); 5.79(d. 1H, J=8,

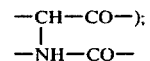

6.80(d. 1H, J=8, pyridine ring proton); 8.38 (d. 1H, J=8, pyridine ring proton); Symmetry center 7.56 (ABq. 4H, tolyl ring proton); Symmetry center 7.07 (ABq. 4H, p-hydroxy phenyl ring proton); 9.35 (d. 1H, J=8,$\underline{H}$ at 7-position); 10.62 (d. 1H, J=7,

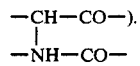

EXAMPLE 8

In 0.615 ml of 0.5 N sodium hydrogen carbonate was dissolved 49.4 mg of 5-mercapto-1,3,4-thiadiazole-2-carboxylic acid amide and 200 mg of 7-{D-(−)-α-[2-hydroxy-6-(p-tolyl)pyridine-3-carbonylamino]-p-hydroxyphenylacetamido}-3-acetoxymethyl-3-cephem-4-carboxylic acid and 0.615 ml of 0.5 N sodium hydrogen carbonate were added and dissolved thereto. The solution was warmed at 65° to 66° C. for 4.5 hours under nitrogen atmosphere. 4 ml of ethanol was added thereto and cooled with ice to give pale yellow crystals, which were filtered and washed with water-containing ethanol and ethanol. Thus obtained was 127 mg of sodium 7-{D(−)-α-[2-hydroxy-6-(p-tolyl)pyridine-3-carbonylamino]-p-hydroxyphenylacetamido}-3-(5-carbamoyl-1,3,4-thiadiazol-2-ylthiomethyl)-3-cephem-4-carboxylate with m.p. 230° to 232° C. (decomp.).

IR spectrum (Nujol) cm$^{-1}$: 1762–1754 (β-lactam), 1679–1663, 1615 (CONH, COO$^\ominus$).

EXAMPLE 9

In 2 ml of water was dissolved 62.6 mg of 2-[N-(2-aminoethyl)-carbamoyl]-5-mercapto-1,3,4-thiadiazole by heating and 200 mg of 7-{D(−)-α-[2-hydroxy-6-(p-tolyl)pyridine-3-carbonylamino]-p-hydroxyphenylacetamido}-3-acetoxymethyl-3-cephem-4-carboxylic acid and 0.615 ml of 0.5 N sodium hydrogen carbonate were added thereto and dissolved. The solution was warmed at 65° to 66° C. for 4.5 hours under nitrogen atmosphere. The solution was cooled with ice to give pale yellow crystals, which were filtered, washed with water and dried. Thus obtained was 145 mg of sodium 7-{D(−)-α-[2-hydroxy-6-(p-tolyl)pyridine-3-carbonylamino]-p-hydroxyphenylacetamido}-3-{5-[N-(2-aminoethyl)carbamoyl]-1,3,4-thiadiazol-2-ylthiomethyl}-3-cephem-4-carboxylate with m.p. 220° to 230° C. (decomp.).

IR spectrum (Nujol) cm$^{-1}$: 1764 (β-lactam), 1658, 1612–1602 (CONH, COO$^\ominus$).

EXAMPLE 10

In 0.615 ml of 0.5 N sodium hydrogen carbonate was dissolved 62 mg of 5-mercapto-2,2'-bis-(1,3,4-thiadiazole) with m.p. 208° to 210° C. and 200 mg of 7-{D(−)-α-[2-hydroxy-6-(p-tolyl)pyridine-3-carbonylamino]-p-hydroxyphenylacetamido}-3-acetoxymethyl-3-cephem-4-carboxylic acid and 0.615 ml of 0.5 N sodium hydrogen carbonate were added thereto and dissolved. The solution was warmed at 65° to 66° C. for 4.5 hours under nitrogen atmosphere. 4 ml of ethanol was added thereto and the mixture was allowed to stand and then cooled gradually with ice. The sodium salt thus obtained was filtered and washed with water-containing ethanol and ethanol. Thus obtained was 145 mg of sodium 7-{D(−)-α-[2-hydroxy-6-(p-tolyl)pyridine-3-carbonylamino]-p-hydroxyphenylacetamido}-3-[2,2'-bis(1,3,4-thiadiazole)-5-ylthiomethyl]-3-cephem-4-carboxylate with m.p. 220° to 230° C. (decomp.).

IR spectrum (Nujol) cm$^{-1}$: 1765 (β-lactam), 1659, 1613–1604 (CONH, COO$^\ominus$).

EXAMPLE 11

In 0.615 ml of 0.5 N sodium hydrogen carbonate was dissolved 63 mg of 2-[N-(2-hydroxyethyl)carbamoyl]-5-mercapto-1,3,4-thiadiazole and 200 mg of 7-{D(−)-α-[2-hydroxy-6-(p-tolyl)pyridine-3-carbonylamino]-p-hydroxyphenylacetamido}-3-acetoxymethyl-3-cephem-4-carboxylic acid and 0.615 ml of 0.5 N sodium hydrogen carbonate were added thereto and dissolved. The mixture was warmed at 65° to 66° C. for 4.5 hours under nitrogen atmosphere. 4 ml of ethanol was added thereto and the mixture was gradually cooled and next cooled with ice to give pale yellow sodium salt, which was filtered and washed with water-containing ethanol and ethanol. Thus obtained was 119 mg of sodium 7-{D(−)-α-[2-hydroxy-6-(p-tolyl)pyridine-3-carboxylamino]-p-hydroxyphenylacetamido}-3-{5-[N-(2-hydroxyethyl)-carbamoyl]-1,3,4-thiadiazole-2-ylthiomethyl}-3-cephem-4-carboxylate with m.p. 220° to 230° C. (decomp.).

IR spectrum (Nujol) cm$^{-1}$: 1760 (β-lactam), 1660, 1612–1603 (CONH, COO$^\ominus$).

EXAMPLE 12

In about 3 ml of water was dissolved 76 mg of 2-mercapto-5-piperazinocarbonyl-1,3,4-thiadiazole with m.p. 243° to 245° C. (decomp.) and 200 mg of 7-{D(−)-α-[2-hydroxy-6-(p-tolyl)pyridine-3-carbonylamino]-p-hydroxyphenylacetamido}-3-acetoxymethyl-3-cephem-4-carboxylic acid and 0.615 ml of 0.5 N sodium hydrogen carbonate were added thereto and dissolved. The mixture was warmed at 65° to 66° C. for 5 hours under nitrogen atmosphere. After the solution was cooled, the pale yellow crystals thus obtained were filtered and washed with ethanol and water. Thus obtained was 126 mg of sodium 7-{D(−)-α-[2-hydroxy-6-(p-tolyl)pyridine-3-carbonylamino]-p-hydroxyphenylacetamido}-3-(5-piperazinocarbonyl-1,3,4-thiadiazol-2-ylthiomethyl)-3-cephem-4-carboxylate with m.p. 220° to 230° C. (decomp.). IR spectrum (Nujol) cm$^{-1}$: 1762 (β-lactam), 1658, 1612 to 1600 (CONH, COO$^\ominus$).

EXAMPLE 13

In 0.614 ml of 0.5 N sodium hydrogen carbonate was dissolved 54 mg of 2-(N-methylcarbamoyl)-5-mercapto-1,3,4-thiadiazole and 200 mg of 7-{D(−)-α-[2-hydroxy-6-(p-tolyl)pyridine-3-carbonylamino]-p-hydroxyphenylacetamido}-3-acetoxymethyl-3-cephem-4-carboxylic acid and 0.614 ml of 0.5 N sodium hydrogen carbonate were added thereto and dissolved. The solution was warmed at 65° to 66° C. for 5 hours under nitrogen atmosphere. 4 ml of ethanol was added thereto and the mixture was gradually cooled and the pale yellow sodium salt thus obtained was filtered and washed with water-containing ethanol and ethanol. Thus obtained was 135 mg of sodium 7{D(−)-α-[2-hydroxy-6-(p-tolyl)pyridine-3-carbonylamino]-p-hydroxyphenylacetamido}-3-[5-(N-methylcarbamoyl)-1,3,4-thiadiazole-2-ylthiomethyl]-3-cephem-4-carboxylate with m.p. 220° to 230° C.

IR spectrum (Nujol) cm$^{-1}$: 1765 (β-lactam), 1658, 1615 (CONH, COO$^\ominus$).

EXAMPLE 14

In 3 ml of water was dissolved 80 mg of 2-[N-(diethylaminoethyl)carbamoyl]-5-mercapto-1,3,4-thiadiazole with m.p. 234° to 235° C. (decomp.) and 200 mg of 7-{D(−)-α-[2-hydroxy-6-(p-tolyl)pyridine-3-carbonylamino]-p-hydroxyphenylacetamido}-3-acetoxymethyl-3-cephem-4-carboxylic acid and 0.614 ml of 0.5 N sodium hydrogen carbonate were added thereto and dissolved. The mixture was warmed at 65° to 66° C. for 4.5 hours under nitrogen atmosphere. The mixture was cooled to give a pale yellow precipitate, which was filtered out and, washed with water and dried. Thus obtained was 128 mg of sodium 7-{D(—)-α-[2-hydroxy-6-(p-tolyl)pyridine-3-carbonylamino]-p-hydroxyphenylacetamido}-3-{5[N-(2-diethylaminoethyl)carbamoyl]-1,3,4-thiadiazol-2-ylthiomethyl}-3-cephem-4-carboxylate with m.p. 200° to 205° C. (decomp.).

IR spectrum (Nujol) cm$^{-1}$: 1765 (β-lactam), 1660, 1613–1600 (CONH, COO$\ominus$).

EXAMPLE 15

In 0.615 ml of 0.5 N sodium hydrogen carbonate was dissolved 67.2 mg of 2-[N-(2-hydroxyethyl)-N-methylcarbamoyl]-5-mercapto-1,3,4-thiadiazole with m.p. 143° to 144° C. (decomp.) and 200 mg of 7-{D(—)-α-[2-hydroxy-6-(p-tolyl)pyridine-3-carbonylamino]-p-hydroxyphenylacetamido}-3-acetoxymethyl-3-cephem-4-carboxylic acid and 0.615 ml of 0.5 N sodium hydrogen carbonate were added thereto. The mixture was warmed at 65° to 66° C. for 4.5 hours under nitrogen atmosphere. 4 ml of ethanol was added and cooled gradually with ice. The sodium salt thus obtained was filtered and washed with water-containing ethanol and ethanol, and dried. Thus obtained was 118 mg of sodium 7-{D(—)-α-[2-hydroxy-6-(p-tolyl)pyridine-3-carbonylamino]-p-hydroxyphenylacetamido}-3-}5-[N-(2-hydroxyethyl)-N-methylcarbamoyl]-1,3,4-thiadiazol-2-ylthiomethyl}-3-cephem-4-carboxylate with m.p. 205° to 215° C.

IR spectrum (Nujol) cm$^{-1}$: 1760 (β-lactam), 1657, 1613–1600 (CONH, COO$\ominus$).

EXAMPLE 16

In 0.615 ml of 0.5 N sodium hydrogen carbonate was dissolved 76.4 mg of 2-{N-[2-(2-hydroxyethoxy)ethyl]carbamoyl}-5-mercapto-1,3,4-thiadiazole with m.p. 129° to 131° C. and 200 mg of 7-{D(—)-α-[2-hydroxy-6-(p-tolyl)pyridine-3-carbonylamino]-p-hydroxyphenylacetamido}-3-acetoxymethyl-3-cephem-4-carboxylic acid and 0.615 ml of 0.5 N sodium hydrogen carbonate were added. The mixture was warmed at 65° to 66° C.for 5 hours under nitrogen atmosphere. 4 ml of ethanol was added and the mixture was cooled with ice to give a sodium salt precipitate, which was filtered out, washed with water-containing ethanol and ethanol, and dried. Thus obtained was 135 mg of sodium 7-{D(—)-α-[2-hydroxy-6-(p-tolyl)pyridine-3-carbonylamino]-p-hydroxyphenylacetamido}-3-{5-((N-[2-(2-hydroxyethoxy)ethyl]carbamoyl))-1,3,4-thiadiazol-2-ylthiomethyl}-3-cephem-4-carboxylate with m.p. 215° to 230° C.

IR spectrum (Nujol) cm$^{-1}$: 1761 (β-lactam); 1660, 1612 to 1603 (CONH, COO$\ominus$).

EXAMPLE 17

In 0.615 ml of 0.5 N sodium hydrogen carbonate was dissolved 76.4 mg of 2-[N,N-bis(2-hydroxyethyl)-carbamoyl]-5-mercapto-1,3,4-thiadiazole with m.p. 132° to 133° C. and 200 mg of 7-{D(—)-α-[2-hydroxy-6-(p-tolyl)pyridine-3-carbonylamino]-p-hydroxyphenylacetamido}-3-acetoxymethyl-3-cephem-4-carboxylic acid and 0.615 ml of 0.5 N sodium hydrogen carbonate were added thereto. The mixture was warmed at 65° to 66° C. for 5 hours under nitrogen atmosphere. 4 ml of ethanol was added thereto and the mixture was cooled with ice to give a sodium salt precipitate, which was filtered out and washed with water-containing ethanol and ethanol, and dried. Thus obtained was 127 mg of sodium 7-{D(—)-α-[2-hydroxy-6-(p-tolyl)pyridine-3-carbonylamino]-p-hydroxyphenylacetamido}-3-{5-[N,N-bis(2-hydroxyethyl)carbamoyl]-1,3,4-thiadiazol-2-ylthiomethyl}-3-cephem-4-carboxylate with m.p. 218° to 230° C.

IR spectrum (Nujol) cm$^{-1}$: 1761 (β-lactam), 1657, 1613 to 1660 (CONH, COO$\ominus$).

EXAMPLE 18

In 0.615 ml of 0.5 N sodium hydrogen carbonate was dissolved 71.5 mg of 2-[N-(3-methoxy-n-propyl)carbamoyl]-5-mercapto-1,3,4-thiadiazole with m.p. 135° to 136° C. and 200 mg of 7-{D(—)-α-[2-hydroxy-6-(p-tolyl)pyridine-3-carbonylamino]-p-hydroxyphenylacetamido}-3-acetoxymethyl-3-cephem-4-carboxylic acid and 0.615 ml of 0.5 N sodium hydrogen carbonate were added thereto. The mixture was warmed at 65° C. for 5 hours under nitrogen atmosphere. 4 ml of ethanol was added thereto and the mixture was gradually cooled to give a sodium salt precipitate, which was filtered out washed with water-containing ethanol and ethanol, and dried. Thus obtained was 138 mg of sodium 7-{D(—)-α-[2-hydroxy-6-(p-tolyl)-pyridine-3-carbonylamino]-p-hydroxyphenylacetamido}-3-{5-[N-(3-methoxy-n-propyl)carbamoyl]-1,3,4-thiadiazol-2-ylthiomethyl}-3-cephem-4-carboxylate with m.p. 220° to 230° C.

IR spectrum (Nujol) cm$^{-1}$: 1760 (β-lactam), 1662, 1613 to 1605 (CONH, COO$\ominus$).

EXAMPLE 19

In 0.615 ml of 0.5 N sodium hydrogen carbonate was dissolved 78 mg of dipotassium 5-mercapto-1,3,4-thiadiazole-2-carbohydroxamate and 200 mg of 7-{D(—)-α-[2-hydroxy-6-(p-tolyl)-pyridine-3-carbonylamino]-p-hydroxyphenylacetamido}-3-acetoxymethyl-3-cephem-4-carboxylic acid and 0.615 ml of 0.5 N sodium hydrogen carbonate were added thereto. The mixture was warmed at 65° to 66° C. for 5 hours under nitrogen atmosphere. 4 ml of ethanol was added thereto and the mixture was gradually cooled to give a potassium salt precipitate, which was filtered out, washed with water-containing ethanol and ethanol, and dried. Thus obtained was 145 mg of potassium 7-{D(—)-α-[2-hydroxy-6-(p-tolyl)pyridine-3-carbonylamino]-p-hydroxyphenylacetamido}-3-[5-(N-hydroxycarbamoyl)-1,3,4-thiadiazol-2-ylthiomethyl]-3-cephem-4-carboxylate (where a sodium salt was contained in part) with m.p. 215° to 230° C.

IR spectrum (Nujol) cm$^{-1}$: 1758 (β-lactam), 1654, 1610 to 1600 (CONH, COO$\ominus$).

EXAMPLE 20

In 30 ml of dichloromethane was suspended 1.067 g of 7-{D(—)-α-amino-p-hydroxyphenylacetamido]-3-acetoxymethyl-3-cephem-4-carboxylic acid trifluoroacetic acid salt and 800 mg of triethylamine, 5 ml of dimethylformamide and 493 mg of p-nitrophenyl 5-hydroxy-3-methylthio-asymmetrical triazine-6-carboxylate. The mixture was stirred at room temperature for 1.5 hours. After reaction, the solvent was evaporated and 5 ml of water and 3 ml of 1 N hydrochloric acid were added to the residue to give raw crystals, which were filtered and washed with water. These crystals were dissolved in 3 ml of 0.5 N sodium hydrogen cabonate and an undissolved substance was filtered. To the filtrate, after it being cooled, was gradually added 1.6 ml of 1 N hydrochloric acid with stirring to give yellow crystals, which was filtered, washed with water and dried. Thus obtained was 640 mg of 7-[D(—)-α-(5-hydroxy-3-methylthio-asymmetrical-triazine-6-carbonylamino)-p-hydroxyphenylacetamido]-3-acetoxymethyl-3-cephem-4-carboxylic acid with m.p. 205° to 220° C. (decomp.).

IR spectrum (Nujol) cm$^{-1}$: 1774 (β-lactam), 1715, 1665, 1614, 1598 (COOH, CONH).

NMR spectrum (DMSO-d$_6$-TSP) δ (ppm): 2.03(s. 3H, —O—COC$\underline{H}_3$); 2.52(s. 3H, —S—C$\underline{H}_3$); 3.49(s. 2H, —C$\underline{H}_2$— at 2-position); symmetrical center 4.85(ABq. 2H, —C$\underline{H}_2$— at 3-position); 5.05(d. 1H, J=5, H at 6-position); 5.73(d.d. 1H, H at 7-position); 5.72(d. 1H, J=7,

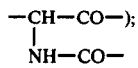

symmetrical center 7.02(ABq. 4H, p-hydroxyphenyl ring proton); 11.0(d. 1H, J=8, H at 7-position); 12.0(d. 1H, J=7,

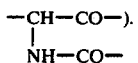

EXAMPLE 21

In 1.18 ml of 0.5 N sodium hydrogen carbonate was dissolved 70 mg of 2-[N-(2-hydroxyethyl)carbamoyl]-5-mercapto-1,3,4-thiadiazole and 200 mg of 7-[D(—)-α-(5-hydroxy-3-methylthio-asymmetrical-triazine-6-carboylamino)-p-hydroxyphenylacetamido]-3-acetoxymethyl-3-cephem-4-carboxylic acid and 29 mg of sodium hydrogen carbonate were added thereto and dissolved. The mixture was warmed at 65° to 66° C. for 5 hours under nitrogen atmosphere. 5 ml of ethanol was added and the mixture was gradually cooled with ice to give a yellow sodium salt, which was filtered, washed with water containing ethanol and ethanol, and dried. Thus obtained was 114 mg of sodium 7-[D(—)-α-(5-hydroxy-3-methylthioasymmetrical-triazine-6-carbonylamino)-p-hydroxyphenylacetamido]-3-{5-[N-(2-hydroxyethyl)carbamoyl]-1,3,4-thiadiazol-2-ylthiomethyl}-3-cephem-4-carboxylate with m.p. 235° to 250° C. (decomp.).

IR spectrum (Nujol) cm$^{-1}$: 1760 (β-lactam), 1656 to 1600 (CONH, COO$^\ominus$).

EXAMPLE 22

In 1.18 ml of 0.5 N sodium hydrogen carbonate was dissolved 69 mg of 5-mercapto-2,2'-bis(1,3,4-thiadiazole) and 200 mg of 7-[D(—)-α-(5-hydroxy-3-methylthio-asymmetricaltriazine-6-carbonylamino)-p-hydroxyphenylacetamido]-3-acetoxymethyl-3-cephem-4-carboxylic acid and 29 mg of sodium hydrogen carbonate were added thereto and dissolved. The mixture was warmed at 65° to 66° C. for 5 hours under nitrogen atmosphere. 5 ml of ethanol was added thereto and the mixture was cooled to give a sodium salt, which was filtered out, washed with water-containing ethanol and ethanol, and dried. Thus obtained was 100 mg of sodium 7-[D(—)-α-(5-hydroxy-3-methylthio-asymmetrical-triazine-6-carbonylamino)-p-hydroxyphenylacetamido]-3-[2,2'-bis(1,3,4-thiadiazol)-5-ylthiomethyl]-3-cephem-4-carboxylate with m.p. 230° to 245° C. (decomp.).

IR spectrum (Nujol) cm$^{-1}$: 1760 (β-lactam), 1651–1600 (CONH, COO$^\ominus$).

EXAMPLE 23

In 1.18 ml of 0.5 N sodium hydrogen carbonate was dissolved 40 mg of 2-mercapto-1,3,4-thiadiazole and 200 mg of 7-[D(—)-α-(5-hydroxy-3-methylthio-asymmetrical-triazine-6-carbonylamino)-p-hydroxyphenylacetamido]-3-acetoxymethyl-3-cephem-4-carboxylic acid and 29 mg of sodium hydrogen carbonate were added thereto and dissolved. The mixture was warmed at 65° to 66° C. for 5 hours under nitrogen atmosphere. 5 ml of ethanol was added thereto and the mixture was cooled to give a sodium salt, which was filtered, washed with water-containing ethanol and ethanol, and dried. Thus, obtained was 115 mg of sodium 7-[D(—)-α-(5-hydroxy-3-methylthio-asymmetrical-triazine-6-carbonylamino)-p-hydroxyphenylacetamido]-3-(1,3,4-thiadiazol-2-ylthiomethyl)-3-cephem-carboxylate with m.p. 235° to 250° C. (decomp.).

IR spectrum (Nujol) cm$^{-1}$: 1760 (β-lactam), 1650 to 1660 (CONH, COO$^\ominus$).

EXAMPLE 24

In 0.63 ml of 0.5 N sodium hydrogen carbonate was dissolved 45.9 mg of 2-mercapto-1,3,4-thiadiazole and 200 mg of 7-{D(—)-α-[2-hydroxy-6-(p-tolyl)pyridine-3-carbonylamino]phenylacetamido}-3-acetoxymethyl-3-cephem-4-carboxylic acid and 0.63 ml of 0.5 N sodium hydrogen carbonate were added thereto and pH of the solution was regulated to 6.4 to 6.6. The mixture was warmed at 64° to 65° C. for 8 hours under nitrogen atmosphere. After reaction, the mixture was filtered while hot and washed with 5 ml of water. To the combined filtrate was added 0.65 ml of 1 N hydrochloric acid with ice-cooling under stirring to give pale yellow crystals, which were filtered out, washed with water and dried. Thus obtained was 135 mg of 7-{D(—)-α-[2-hydroxy-6-(p-tolyl)pyridine-3-carbonylamino]phenylacetamido}-3-(1,3,4-thiadiazol-2-ylthiomethyl)-3-cephem-4-carboxylic acid with m.p. 186° to 190° C. (decomp.).

IR spectrum (Nujol) cm$^{-1}$: 1780 (β-lactam), 1655 (amide)

EXAMPLE 25

In 0.63 ml of 0.5 N sodium hydrogen carbonate was dissolved 61.9 mg of 3-mercapto-5-carboxymethyl-1,2,4-triazole with m.p. 220° C. and 200 mg of 7-{D(—)-α-[2-hydroxy-6-(p-tolyl)pyridine-3-carbonylamino]phenylacetamido}-3-acetoxymethyl-3-cephem-4-carboxylic acid and 0.63 ml of 0.5 N sodium hydrogen carbonate were added thereto and the solution was adjusted to pH 6.4 to 6.6. The solution was warmed at 64° to 65° C. for 6 hours under nitrogen atmosphere. After reaction, 0.65 ml of 1 N hydrochloric acid was added thereto with ice-cooling with stirring to give crystals, which were filtered, washed with water and dried. Thus obtained was 124 mg of 7-{D(—)-α-[2-hydroxy-6-(p-tolyl)pyridine-3-carbonylamino]phenylacetamido}-3-(5-carboxymethyl-1,2,4-triazol-3-ylthiomethyl)-3-cephem-4-carboxylic acid with m.p. 178° to 185° C. (decomp.).

IR spectrum (Nujol) cm$^{-1}$: 1775 (β-lactam), 1655 (amide)

EXAMPLE 26

In 0.95 ml of 0.5 N sodium hydrogen carbonate was dissolved 61.8 mg of 3-mercapto-4-N-methyl-5-carboxymethyl-1,2,4-triazole and 200 mg of 7-{(—)-α-[2-hydroxy-6-(p-tolyl)pyridine-3-carbonylamino]-phenylacetamido}-3-acetoxymethyl-3-cephem-4-carboxylic acid and 0.95 ml of 0.5 N sodium hydrogen carbonate were added thereto. The mixture was warmed at 65° to 66° C. for 8 hours under nitrogen atmosphere. The undissolved substance was filtered and 0.95 ml of 1 N hydrochloric acid was added to the filtrate with ice-cooling under stirring to give pale yellow crystals, which were filtered, washed with water and dried. Thus obtained was 135 mg of 7-{D(—)-α-[2-hydroxy-6-(p-tolyl)pyridine-3-carbonylamino]-phenylacetamido}-3-(4-methyl-5-carboxymethyl-1,2,4-triazole-3-ylthiomethyl)-3-cephem-4-carboxylic acid with 185° C. to 189° C. (decomp.).

IR spectrum (Nujol) cm$^{-1}$: 1775 (β-lactam), 1655 (amide).

EXAMPLE 27

To a solution of 67.4 mg of 3-mercapto-5-carboxyethyl-1,2,4-triazole in 0.95 ml of 0.5 N sodium hydrogen carbonate was added a solution of 200 mg of 7-{D(—)-α-[2-hydroxy-6-(p-tolyl)pyridine-3-carbonylamino]-phenylacetamido}-3-acetoxymethyl-3-cephem-4-carboxylic acid in 0.95 ml of 0.5 N sodium hydrogen carbonate. The solution was warmed at 65° to 66° C. for 6 hours under nitrogen atmosphere. After reaction, 0.65 ml of 1 N hydrochloric acid was added slowly with ice-cooling under nitrogen atmosphere to give pale yellow crystals, which were filtered, washed with a small amount of water and dried. Thus obtained was 130 mg of 7-{D(—)-α-[2-hydroxy-6-(p-tolyl)pyridine-3-carbonylamino]phenylacetamido}-3-[5-(2-carboxyethyl)-1,2,4-triazole-3-ylthiomethyl$\pi$-3-cephem-4-carboxylic acid with m.p. 162° to 170° C. (decomp.).

IR spectrum (Nujol) cm$^{-1}$: 1775 (β-lactam), 1655 (amide).

EXAMPLE 28

In 1.28 ml of 0.5 N sodium hydrogen carbonate were suspended 55.2 mg of 2-mercapto-1,3,4-oxadiazole-5-carboxamide and 200 mg of 7-{D(—)-α-[2-hydroxy-6-(p-tolyl)pyridine-3-carbonylamino]phenylacetamido}-3-acetoxymethyl-3-cephem-4-carboxylic acid. The mixture was warmed at 65° to 66° C. for 9 hours with stirring under nitrogen atmosphere. After reaction, 0.65 ml of 1 N hydrochloric acid was added to the reaction mixture with ice-cooling under stirring to give crystals, which were filtered, washed with water and dried. Thus obtained was 158 mg of 7-{D(—)-α-[2-hydroxy-6-(p-tolyl)pyridine-3-carbonylamino]phenylacetamido}-3-(5-carbamoyl-1,3,4-oxadiazole-2-ylthiomethyl)-3-cephem-4-carboxylic acid with m.p. 170° to 175° C. (decomp.).

IR spectrum (Nujol) cm$^{-1}$: 1780 (β-lactam), 1660 (amide).

EXAMPLE 29

In 1.28 ml of 0.5 N sodium hydrogen carbonate were suspended 51.1 mg of 2-mercapto-5-(N-methylcarbamoyl)-1,3,4-oxadiazole and 200 mg of 7-{D(—)-α-[2-hydroxy-6-(p-tolyl)pyridine-3-carbonylamino]-phenylacetamido}-3-acetoxymetnyl-3-cephem-4-carboxylic acid. The mixture was warmed at 65° to 66° C. for 9 hours with stirring under nitrogen atmosphere. After reaction, 0.65 ml of 1 N hydrochloric acid was added to the reaction mixture with ice-cooling under stirring to give crystals, which were filtered, washed with water and dried. Thus obtained was 161 mg of 7-{D(—)-α-[2-hydroxy-6-(p-tolyl)pyridine-3-carbonylamino]phenylacetamido}-3-{5-(N-methylcarbamoyl)-1,3,4-oxadiazole-2-ylthiomethyl}-3-cephem-4-carboxylic acid with m.p. 165° to 173° C. (decomp.).

IR spectrum (Nujol) cm$^{-1}$: 1775 (β-lactam), 1655 (amide).

EXAMPLE 30

In 0.63 ml of 0.5 N sodium hydrogen carbonate was dissolved 44.8 mg of 2-mercapto-1,3,4-thiadiazole and a solution of 200 mg of 7-{p-hydroxy-D-(—)-α-[2-hydroxy-6-(p-tolyl)pyridine-3-carbonylamino]-phenylacetamido}-3-acetoxymethyl-3-cephem-4-carboxylic acid in 0.63 ml of 0.5 N sodium hydrogen carbonate was added thereto. The solution was regulated to pH 6.4 to 6.6 and warmed at 64° to 65° C. for 8 hours under nitrogen atmosphere. After reaction, the reaction mixture was filtered while hot and washed with 5 ml of water. To the combined filtrate was added 0.64 ml of 1 N hydrochloric acid with ice-cooling under stirring to give pale yellow crystals, which were filtered, washed with water and dried. Thus obtained was 142 mg of 7-{p-hydroxy-D(—)-α-[2-hydroxy-6-(p-tolyl)pyridine-3-carbonylamino]phenylacetamido}-3-(1,3,4-thiadiazole-2-ylthiomethyl)-3-cephem-4-carboxylic acid with m.p. 194° to 198° C. (decomp.).

IR spectrum (Nujol) cm$^{-1}$: 1780 (β-lactam), 1655 (amide).

EXAMPLE 31

A solution of 42 mg of 2-mercapto-5-methyl-1,3,4-thiadiazole in 0.63 ml of 0.5 N sodium hydrogen carbonate and a solution of 200 mg of 7-{p-hydroxy-D(—)-α-[2-hydroxy-6-(p-tolyl)-pyridine-3-carbonylamino]-phenylacetamido}-3-acetoxymethyl-3-cephem-4-carboxylic acid in 0.63 ml of 0.5 N sodium hydrogen carbonate were combined and adjusted to pH 6.4 to 6.6.

The solution was warmed at 64° to 65° C. for 9 hours with stirring under nitrogen atmosphere. The reaction mixture was filtered while hot and 0.64 ml of 1 N hydrochloric acid was added to the filtrate with ice-cooling to give pale yellow crystals, which were filtered washed with water and dried. Thus obtained was 150 mg of 7-}p-hydroxy-D(—)-α-[2-hydroxy-6-(p-tolyl)pyridine-3-carboxylamino]phenylacetamido}-3-(5-methyl-1,3,4-thiadiazole-2-ylthiomethyl-3-cephem-4-carboxylic acid with m.p. 175° to 179° C. (decomp.).

IR spectrum (Nujol) cm$^{-1}$: 1775 (β-lactam), 1660 (amide).

EXAMPLE 32

In 0.95 ml of 0.5 N sodium hydrogen carbonate was dissolved 60.1 mg of 3-mercapto-5-carboxymethyl-1,2,4-triazole with m.p. 220° C. and 200 mg of 7-{p-hydroxy-D(—)-α-[2-hydroxy-6-(p-tolyl)pyridine-3-carbonylamino]phenylacetamido}-3-acetoxymethyl-3-cephem-4-carboxylic acid and 0.95 ml of 0.5 N sodium hydrogen carbonate were added thereto and the solution was adjusted to pH 6.4 to 6.6. The solution was warmed at 64° to 65° C. for 6 hours under nitrogen atmosphere. After reaction, 0.95 ml of 1 N hydrochloric acid was added gradually to the solution with ice-cooling under stirring to give crystals, which were filtered, washed with water and dried. Thus obtained was 182 mg of 7-{p-hydroxy-D(—)-α-[2-hydroxy-6-(p-tolyl)-pyridine-3-carbonylamino]phenylacetamido}-3-(5-carboxymethyl-1,2,4-triazole-2-ylthiomethyl)-3-cephem-4-carboxylic acid with m.p. 185° to 195° C. (decomp.).

IR spectrum (Nujol) cm$^{-1}$: 1775 (β-lactam), 1665 (amide).

EXAMPLE 33

To a solution of 55 mg of 3-mercapto-4-N-methyl-5-carboxymethyl-1,2,4-triazole in 0.95 ml of 0.5 N sodium hydrogen carbonate was added a solution of 200 mg of 7-{p-hydroxy-D(—)-α-[2-hydroxy-6-(p-tolyl)pyridine-3-carbonylamino]phenylacetamido}-3-acetoxymethyl-3-cephem-4-carboxylic acid in 0.95 ml of 0.5 N sodium hydrogen carbonate. The solution was regulated to pH 6.4 to 6.6 and warmed at 64° to 65° C. for 8 hours under nitrogen atmosphere. The undissolved substance was filtered out and 0.95 ml of 1 N hydrochloric acid was added to the filtrate with ice-cooling with stirring to give pale yellow crystals, which were filtered out, washed with water and dried. Thus obtained was 148 mg of 7-{p-hydroxy-D(—)-α-[2-hydroxy-6-(p-tolyl)-pyridine-3-carbonylamino]-phenylacetamido}-3-(4-methyl-5-carboxymethyl-1,2,4-triazole-3-ylthiomethyl)-3-cephem-4-carboxylic acid with m.p. 184° to 190° C. (decomp.).

IR spectrum (Nujol) cm$^{-1}$: 1770 (β-lactam), 1650 (amide).

EXAMPLE 34

To a solution of 66 mg of 3-mercapto-5-carboxyethyl-1,2,4-triazole in 0.95 ml of 0.5 N sodium hydrogen carbonate was added a solution of 200 mg of 7-{p-hydroxy-D(—)-α-[2-hydroxy-6-(p-tolyl)pyridine-3-carbonylamino]phenylacetamido}-3-acetoxymethyl-3-cephem-4-carboxylic acid in 0.95 ml of 0.5 N sodium hydrogen carbonate. The solution was warmed at 65° to 66° C. for 6 hours under nitrogen atmosphere. 0.95 ml of 1 N hydrochloric acid was gradually added with ice-cooling to give pale yellow crystals, which were filtered and washed with a small amount of water and dried. Thus obtained was 180 mg of 7-{p-hydroxy-D(—)-α-[2-hydroxy-6-(p-tolyl)pyridine-3-carbonylamino]phenylacetamido}-3[5-(2-carboxyethyl-1,2,4-triazole-3-ylthiomethyl]-3-cephem-4-carboxylic acid with m.p. 175° to 185° C. (decomp.).

IR spectrum (Nujol) cm$^{-1}$: 1775 (β-lactam), 1655 (amide).

EXAMPLE 35

A suspension of 55 mg of 2-mercapto-1,3,4-oxadiazole-5-carboxamide and 200 mg of 7-{p-hydroxy-D(—)-α-[2-hydroxy-6-(p-tolyl)pyridine-3-carbonylamino]phenylacetamido}-3-acetoxymethyl-3-cephem-4-carboxylic acid in 1.25 ml of 0.5 N sodium hydrogen carbonate was warmed at 65° to 66° C. for 9 hours with stirring under nitrogen atmosphere. After reaction, 0.65 ml of 1 N hydrochloric acid was added with ice-cooling under stirring to give crystals, which were filtered, washed with water and dried. Thus obtained was 170 mg of 7-{p-hydroxy-D(—)-α-[2-hydroxy-6-(p-tolyl)pyridine-3-carbonylamino]-phenylacetamido}-3-(5-carbamoyl-1,3,4-oxadiazole-2-ylthiomethyl)-3-cephem-4-carboxylic acid with m.p. 187° to 194° C. (decomp.).

IR spectrum (Nujol) cm$^{-1}$: 1780 (β-lactam), 1660 (amide).

EXAMPLE 36

A suspension of 50 mg of 2-mercapto-5-(N-methylcarbamoyl-1,3,4-oxadiazole and 200 mg of 7-{p-hydroxy-D(—)-α-[2-hydroxy-6-(p-tolyl)pyridine-3-carbonylamino]phenylacetamido}-3-acetoxymethyl-3-cephem-4-carboxylic acid in 1.25 ml of 0.5 N sodium hydrogen carbonate was warmed at 65° to 66° C. for 9 hours with stirring under nitrogen atmosphere. After reaction, 0.65 ml of 1 N hydrochloric acid was added with ice-cooling under stirring to give crystals, which were filtered, washed with water and dried. Thus obtained was 195 mg of 7-{p-hydroxy-D(—)-α-[2-hydroxy-6-(p-tolyl)pyridine-3-carbonylamino]-phenylacetamido}-3-{5-(N-methylcarbamoyl)-1,3,4-oxadiazole-2-ylthiomethyl}-3-cephem-4-carboxylic acid with m.p. 185° to 195° C. (decomp.).

IR spectrum (Nujol) cm$^{-1}$: 1775 (β-lactam), 1655 (amide).

EXAMPLE 37

In 30 ml of dichloromethane was suspended 2.82 g of 7-[D-(—)-α-amino-p-hydroxyphenylacetamido]-3-acetoxymethyl-3-cephem-4-carboxylic acid trifluoroacetic acid salt and 2.15 g of triethylamine and 1.25 g of 3,5-dihydroxy-as-triazine-6-carboxylic acid p-nitrophenyl ester in succession were added to the mixture. The mixture was stirred at room temperature for 1.5 hours and was treated in the same manner as in Example 20 to give 2.54 g of 7-[D-(—)-α-(3,5-dihydroxy-as-triazine-6-carboxylamino)-p-hydroxyphenylacetamido]-3-acetoxymethyl-3-cephem-4-carboxylic acid with m.p. 225° to 230° C. (decomp.).

IR spectrum (Nujol) cm$^{-1}$: 1660 (β-lactam), 1665 (CONH)

NMR spectrum (DMSO-d$_6$-TSP)δ(ppm): 2.035(s. 3H, —O—COC$\underline{H}_3$); Symmetric center 4.86(ABq. 2H, —C$\underline{H}_2$— at 3-position); Symmetric center 7.03(ABq. 4H, proton in p-hydroxyphenyl ring).

EXAMPLE 38

200 mg of the compound obtained by Example 37 and 63.2 mg of 2-carbamoyl-5-mercapto-1,3,4-thiadiazole were reacted and treatedd in the same way as in Example 21 to obtain 115 mg of sodium 7-[D-(—)-α-(3,5-dihydroxy-as-triazine-6-carbonylamino)-p-hydroxyphenylacetamido]-3-(5-carbamoyl-1,3,4-thiadiazol-2-ylthiomethyl)-3-cephem-4-carboxylate with m.p. 225°-260° C. (decomp.).

IR spectrum (Nujol) cm$^{-1}$: 1660 (β-lactam); 1666 (CONH)

EXAMPLE 39

200 mg of the compound obtained by Example 37 and 68.7 mg of 2-(N-methylcarbamoyl)-5-mercapto-1,3,4-thiadiazole were reacted and treated in the same way as in Example 21 to give sodium 7-[D-(—)-α-(3,5-dihydroxy-as-triazine-6-carbonylamino)-p-hydroxyphenylacetamido]-3-[5-(N-methylcarbamoyl)-1,3,4-thiadiazol-2-ylthiomethyl]-3-cephem-4-carboxylate with m.p. 255°-260° C. (decomp.).

IR spectrum (Nujol) cm$^{-1}$: 1660 (β-lactam); 1666 (CONH)

EXAMPLE 40

200 mg of the compound obtained by Example 37 and 46 mg of 2-mercapto-1,3,4-thiadiazol were reacted and treated in the same way as in Example 21 to give 92 mg of sodium 7[D-(—)-α-(3,5-dihydroxy-as-triazine-6-carbonylamino)-p-hydroxyphenylacetamido]-3-(1,3,4-thiadiazol-2-ylthiomethyl)-3-cephem-4-carboxylate with m.p. 255°–260° c. (decomp.).

IR spectrum (Nujol) cm$^{-1}$: 1760 (β-lactam); 1655, 1663 (CONH).

EXAMPLE 41

200 mg of the compound obtained by Example 37 and 80.5 mg of 2-[N-(2-hydroxyethyl)carbamoyl]-5-mercapto-1,3,4-thiadiazole were reacted and treated in the same way as in Example 21 to obtain 122 mg of sodium 7-[D-(—)-α-(3,5-dihydroxy-as-triazine-6-carbonylamino)-p-hydroxyphenylacetamido]-3-{5[N-(2-hydroxyethyl)carbamoyl]-1,3,4-thiadiazol-2-ylthiomethyl}-3-cephem-4-carboxylate with m.p. 255° to 260° C. (decomp.).

IR spectrum (Nujol) cm$^{-1}$: 1760 (β-lactam); 1653, 1664 (CONH).

EXAMPLE 42

200 mg of the compound obtained by Example 37 and 79.4 mg of 5-mercapto-2,2'-bis(1,3,4-thiadiazol) were reacted and treated in the same way as in Example 21 to give 125 mg of sodium 7-[D-(—)-α-(3,5-dihydroxy-as-triazine-6-carbonylamino)-p-hydroxyphenylacetamido]-3-[2,2'-bis(1,3,4-thiadiazol)-5-ylthiomethyl]-3-cephem-4-carboxylate with m.p. 245° to 250° C. (decomp.).

IR spectrum (Nujol) cm$^{-1}$: 1660 (β-lactam); 1665 (CONH)

EXAMPLE 43

200 mg of the compound obtained by Example 37 and 73 mg of 3-(1-aminoisoamyl)-5-mercapto-1,2,4-triazole were dissolved and heated for 4.5 hours in 0.715 ml of 0.5 N sodium hydrogen carbonate and 3 ml of water to give crystals, which were filtered after cooling, washed with water and dried to give 154 mg 7-[D-(—)-α-(3,5-dihydroxy-as-triazine-6-carbonylamino)-p-hydroxyphenylacetamido]-3-[5-(1-aminoisoamyl)-1,2,4-triazol-3-ylthiomethyl]-3-cephem-4-carboxylic acid with m.p. 225°–240° C. (decomp.).

IR spectrum (Nujol) cm$^{-1}$: 1659 (β-lactam); 1702, 1658 (CONH)

EXAMPLE 44

200 mg of the compound obtained by Example 37 and 56.6 mg of 3-(1-aminoethyl)-5-mercapto-1,2,4-triazole were reacted and treated in the same way as in Example 43 to give 111 mg of 7-[D-(—)-α-(3,5-dihydroxy-as-triazine-6-carbonylamino)-p-hydroxyphenylacetamido]-3-[5-(1-aminoethyl)-1,2,4-triazol-3-ylthiomethyl]-3-cephem-4-carboxylic acid with m.p. 235° to 250° C. (decomp.).

IR spectrum (Nujol) cm$^{-1}$: 1759 (β-lactam); 1700, 1654 (CONH).

EXAMPLE 45

200 mg of the compound obtained by Example 37 and 35 mg of 3-aminomethyl-5-mercapto-1,2,4-triazole were reacted and treated in the same way as in Example 43 to give 118 mg of 7-[D-(—)-α-(3,5-dihydroxy-as-triazine-6-carbonylamino)-p-hydroxyphenylacetamido]-3-[5-aminomethyl-1,2,4-triazol-3-ylthiomethyl]-3-cephem-4-carboxylic acid with m.p. 245° to 260° C. (decomp.).

IR spectrum (Nujol) cm$^{-1}$: 1759 (β-lactam); 1700, 1655 (CONH)

EXAMPLE 46

200 mg of the compound obtained by Example 37 and 98 mg of 2-[N,N-bis(2-hydroxyethyl)carbamoyl]-5-mercapto-1,3,4-thiadiazole were reacted and treated in the same way as in Example 21 to give 134 mg of sodium 7-[D-(—)-α-(3,5-dihydroxy-as-triazine-6-carbonylamino)-p-hydroxyphenylacetamido]-3-{5-[N,N-bis(2-hydroxyethyl)carbamoyl]-1,3,4-thiadiazol-2-ylthiomethyl}-3-cephem-4-carboxylate with m.p. 245° to 260° C. (decomp.).

IR spectrum (Nujol) cm$^{-1}$: 1660 (β-lactam); 1655 (amide)

EXAMPLE 47

200 mg of the compound obtained by Example 37 and 97.8 mg of 2-{N-[2-(2-hydroxyethoxy)ethyl]carbamoyl}-5-mercapto-1,3,4-thiadiazole were reacted and treated in the same way as in Example 21 to give 127 mg of sodium 7-[D-(—)-α-(3,5-dihydroxy-as-triazine-6-carbonylamino)-p-hydroxyphenylacetamido]-3-{5-((N-[2-(2-hydroxyethyl)ethyl]carbamoyl))-1,3,4-thiadiazol-2-ylthiomethyl}-3-cephem-4-carboxylate with m.p. 250° to 260° C. (decomp.).

IR spectrum (Nujol) cm$^{-1}$: 1763 (β-lactam); 1656, 1655 (CONH).

EXAMPLE 48

200 mg of the compound obtained by Example 37 and 56.5 mg of 3-(1-aminoethyl)-5-mercapto-4-methyl-1,2,4-triazole were reacted and treated in the same way as in Example 43 to give 104 mg of 7-[D-(—)-α-(3,5-dihydroxy-as-triazine-6-carbonylamino)-p-hydroxyphenylacetamido]-3-[5-(1-aminoethyl)-4-methyl-1,2,4-triazol-3-ylthiomethyl]-3-cephem-4-carboxylic acid with m.p. 245°–250° C. (decomp.).

IR spectrum (Nujol) cm$^{-1}$: 1759 (β-lactam); 1700, 1655 (CONH).

EXAMPLE 49

200 mg of the compound obtained by Example 37 and 62 mg of 3-carboxymethyl-5-mercapto-4-methyl-1,2,4-triazole were reacted and treated in the same way as in Example 21 to obtain 98 mg of disodium 7-[D-(—)-α-(3,5-dihydroxy-as-triazine-6-carbonylamino)-p-hydroxyphenylacetamido]-3-[5-carboxymethyl-4-methyl-1,2,4-triazol-3-ylthiomethyl]-3-cephem-4-carboxylate with m.p. 255° to 260° C. (decomp.).

IR spectrum (Nujol) cm$^{-1}$: 1760 (β-lactam); 1656, 1666 (CONH)

EXAMPLE 50

In 1 ml of dimethylformamide was suspended 608 mg of 7-[D-(—)-α-aminophenylacetamido]-3-acetoxymethyl-3-cephem-4-carboxylic acid and 152 mg of triethylamine, 6 ml of dichloromethane and 410 mg of 3-(1-pyrazolyl)-5-hydroxy-as-triazine-6-carboxylic acid p-nitrophenyl ester in succession were added to the suspension under ice-cooling. The mixture was stirred under ice-cooling for 10 minutes and at room temperature for 45 minutes and treated in the same way as in Example 20 to give 907 mg of 7-{D-(—)-α-[3-(1-pyrazolyl)-5-hydroxy-as-triazine-6-carbonylamino]-phenylacetamido}-3-acetoxymethyl-3-cephem-4-carboxylic acid with m.p. 210° to 220° C. (decomp.).

IR spectrum (Nujol) cm$^{-1}$: 1777 (β-lactam); 1745 (CONH).

NMR spectrum (DMSO-d₆-TSP) δ (ppm): 2.03(s. 3H, —O—COC$\underline{H}$₃); 3.50(br. 2H, —C$\underline{H}$₂ at 2-position); 6.77 (q. 1H, proton at pyrazole ring); 7.46(m. 5H, proton at phenyl ring); 7.43 (d. 1H, J=1.5 Hz, proton at pyrazole ring); 8.61(d. 1H, J=3, Hz, proton at pyrazole ring).

EXAMPLE 51

200 mg of the compound obtained by Example 50 and 43.6 mg of 2-mercapto-1,3,4-thiadiazole were reacted and treated in the same way as in Example 21 to give 184 mg of sodium 7-{D-(−)-α-[3-(1-pyrazolyl)-5-hydroxy-as-triazine-6-carbonylamino]-phenylacetamido}-3-(1,3,4-thiadiazol-2-ylthiomethyl)-3-cephem-4-carboxylate with 230° to 240° C. (decomp.).

IR spectrum (Nujol) cm⁻¹: 1756 (β-lactam); 1662 (CONH)

EXAMPLE 52

200 mg of the compound obtained by Example 50 and 59.2 mg of 2-carbamoyl-5-mercapto-1,3,4-thiadiazol were reacted and treated in the same way as in Example 21 to give 162 mg of sodium 7-{D-(−)-α-[3-(1-pyrazolyl)-5-hydroxy-as-triazine-6-carbonylamino]-phenylacetamido}-3-(5-carbamoyl-1,3,4-thiadiazol-2-ylthiomethyl)-3-cephem-4-carboxylate with m.p. 250° to 255° C. (decomp.).

IR spectrum (Nujol) cm⁻¹: 1755 (β-lactam); 1665 (CONH)

EXAMPLE 53

In 4 ml. of a phosphate buffer solution (pH 6.8) were dissolved 180 mg. of 2-mercapto-5-(N-methyl-piperadinocarbonyl)-1,3,4-thiadiazole melting at 243° to 244° C. (decomp.) and 114 mg. of sodium bicarbonate (NaHCO₃), and 400 mg. of 7-{D-(−)-α-[2-hydroxy-6-(p-tolyl)pyridine-3-carbonylamino]-p-hydroxyphenylacetamido}-3-acetoxymethyl-3-cephem-4-carboxylic acid was added to the mixture and dissolved, and then the resulting mixture was heated at 67° to 68° C. in a stream of nitrogen for 4 hours. After cooling the precipitate was filtered and washed sufficiently with water. The thus obtained sodium salt of the desired product was supended in 5 ml. of water, and 1 N-HCl was added thereto to adjust the pH value to 2. The precipitated crystals were filtered and washed sufficiently with water to give 380 mg. of 7-{D-(−)-α-[2-hydroxy-6-(p-tolyl)pyridine-3-carbonylamino]-p-hydroxyphenylacetamido}-3-[5-(N-methyl-piperadinocarbonyl)-1,3,4-thiadiazole-2-ylthiomethyl)]-3-cephem-4-carboxylic acid.

NMR spectrum (DMSO-d₆-TMS) δ (ppm): 10.60 (1H, d, J=6 Hz

—CH—CO—);
|
NH—CO—

7.54 (2H, ABq., J=8 Hz, proton at pyridine ring); 7.50 (4H, ABq., J=8 Hz, proton at tolyl ring); 6.99 (4H, ABq., J=8 Hz, proton at p-hydroxyphenyl ring); 5.70 (1H, dd, H at 7-position); 5.03 (1H, d, J=4 Hz, H at 6-position); 2.90 (4H, broad s,

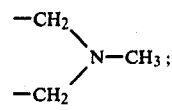

2.50 (3H, s,

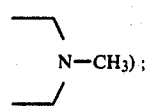

2.37 (3H, s, tolyl-C$\underline{H}$₃).

IR spectrum (Nujol) cm⁻¹: 1764 (β-lactam), 1658 (CONH)

EXAMPLE 54

In 4 ml. of a phosphate buffer solution (pH 6.8) were dissolved 139.5 mg. of 2-mercapto-5-(N,N-dimethylcarbamoyl)-1,3,4-thiadiazole melting at 235° C. (decomp.) and 114 mg. of sodium bicarbonate, and 400 mg. of 7-{D-(−)-α-[2-hydroxy-6-(p-tolyl)pyridine-3-carbonylamino]-p-hydroxyphenylacetamido}-3-acetoxymethyl-3-cephem-4-carboxylic acid was added thereto and dissolved, and then the resulting mixture was heated at 67° to 68° C. in a stream of nitrogen for 4 hours. The precipitated sodium salt of the desired product was filtered and washed sufficiently with water, and 1 N-HCl was added thereto to adjust the pH value of 2. The precipitated free acid was filtered and washed sufficiently with water to give 354 mg. of 7-{D-(−)-α-[2-hydroxy-6-(p-tolyl)pyridine-3-carbonylamino]-p-hydroxyphenylacetamido}-3-[5-(N,N-dimethylcarbamoyl)-1,3,4-thiadiazole-2-ylthiomethyl)]-3-cephem-4-carboxylic acid.

NMR spectrum (DMSO-d₆-TMS) δ (ppm): 10.59 (1H, d, J=8 Hz,

—CH—CO—);
|
NH—CO—

7.55 (2H, ABq., J=8 Hz, proton at pyridine ring); 7.53 (4H, ABq., J=8 Hz, proton at tolyl ring); 7.03 (4H, ABq., J=8 Hz proton at p-hydroxyphenyl ring); 5.70 (1H, dd, H at 7-position); 5.07 (1H, d, J=4 Hz, H at 6-position); 3.65 (2H, broad s, C$\underline{H}$₂ at 2-position); 3.39 and 3.06 (6H, s,

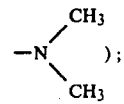

2.37 (3H, s, tolyl-C$\underline{H}$₃).

IR spectrum (Nujol) cm⁻¹: 1775 (β-lactam); 1721, 1688, 1657 (COOH, CONH, CON<)

EXAMPLE 55

In 4 ml. of a phosphate buffer solution (pH 6.8) were dissolved 117 mg. of 2-mercapto-5-piperidinocarbonyl-1,3,4-thiadiazole melting at 234° to 235° C. (decomp.) and 114 mg. of sodium bicarbonate, and 400 mg. of 7-{D-(−)-α-[2-hydroxy-(p-tolyl)-pyridine-3-carbonylamino]-p-hydroxyphenylacetamido}-3-acetoxymethyl-3-cephem-4-carboxylic acid was added thereto and dissolved, and then the resulting mixture was heated at 67° to 68° C. in a stream of nitrogen for 4 hours. After cooling, the precipitated sodium salt of the desired product was filtered and washed with water, and was suspended in 5 ml. of water. Then, 1 N-HCl was added to the suspension to adjust the pH value to 2. Further, the free acid was filtered and washed with water to give 290 mg. of 7-{D-(−)-α-[2-hydroxy-6-(p-tolyl)pyridine-3-carbonylamino]-p-hydroxyphenyl}-3-(5-piperidinocarbonyl-1,3,4-thiadiazole-2-ylthiomethyl)-3-cephem-4-carboxylic acid.

NMR spectrum (DMSO-d$_6$-TMS) δ (ppm): 10.60 (1H, d, J=8 Hz,

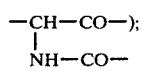

7.57 (2H, ABq., J=8 Hz, proton at pyridine ring); 7.55 (4H, ABq., J=8 Hz, proton at tolyl ring); 7.03 (4H, ABq., J=8 Hz, proton at p-hydroxyphenyl ring); 5.77 (1H, d, J=4 Hz, H at 7-position); 5.07 (1H, d, J=4 Hz, H at 6-position); 3.65 (4H, broad s,

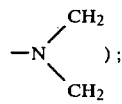

3.97 (2H, broad s, C$\underline{H}_2$ at 2-position); 2.38 (3H, s, tolyl-C$\underline{H}_3$); 1.60 (6H, broad s,

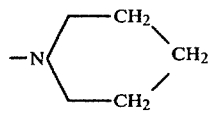

IR spectrum (Nujol) cm$^{-1}$: 1777 (β-lactam); 1722, 1702, 1659 (COOH), CONH, CON<)

EXAMPLE 56

Method A

In 5 ml. of water was suspended 308 mg. of 7-{D-(−)-α-[2-hydroxy-6-(p-tolyl)pyridine-3-carbonylamino]-p-hydroxyphenylacetamido}-3-acetoxymethyl-3-cephem-4-carboxylic acid and 100 mg. of sodium bicarbonate was added thereto and dissolved, and then 64 mg. of 5-mercapto-1-methyl-1H-1,2,3,4-tetrazole was added further thereto. The resulting mixture was heated at 65° C. for 8 hours and passed through a column packed with resin HP-50 to give 103 mg. of a sodium salt of 7-{D-(−)-α-[2-hydroxy-6-(p-tolyl)pyridine-3-carbonylamino]-p-hydroxyphenylacetamido}-3-(1-methyl-1,2,3,4-tetrazole-5-ylthiomethyl)-3-cephem-4-carboxylic acid melting at 185° to 190° C. (decomp.).

NMR spectrum (DMSO-d$_6$-TMS) δ (ppm): 10.60 (1H, d, J=7 Hz,

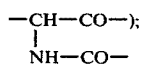

9.30 (1H, d, J=7 Hz, N$\underline{H}$ at 7-position); 8.40 (1H, d, J=8 Hz, proton at pyridine ring); 7.80 (2H, d, proton at toluene ring); 7.40 (4H, m, J=8 Hz, proton at toluene ring, proton at p-hydroxyphenyl ring); 5.75 (1H, d, J=7 Hz,

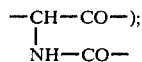

5.60 (1H, dd, H at 7-position); 4.92 (1H, d, J=5 Hz, H at 6-position); 4.35 (2H, ABq., C$\underline{H}_2$ at 3-position); 3.95 (3H, s, N—C$\underline{H}_3$); 2.40 (3H, s, tolyl-C$\underline{H}_3$); 3.50 (2H, ABq., C$\underline{H}_2$ at 2-position).

IR spectrum (Nujol) cm$^{-1}$: 1760 (β-lactam); 1658 (CONH); 1605 (COO$^\ominus$).

Method B

In 8.4 ml. of anhydrous methylene chloride and 8.4 ml. of anhydrous dimethylformamide were dissolved 1.39 g. of trifluoroacetate of 7-{D-(−)-α-amino-p-hydroxyphenylacetamido}-3-(1-methyl-1,2,3,4-tetrazole-5-ylthiomethyl)-3-cephem-4-carboxylic acid, and 0.86 ml. of triethylamine and 830 mg. of p-nitrophenyl ester of 2-hydroxy-6-(p-tolyl)pyridine-3-carboxylic acid were added thereto and then reacted at room temperature for 18 hours. After reaction, insoluble substances were removed by filteration and the filtrate was concentrated to dryness. To the thus obtained syrup was added 10 ml. of 1 N-HCl, and the precipitated crystal was collected by filtration and washed with water and ether. After washing, the crystal was converted to a sodium salt of the desired product by adding sodium bicarbonate thereto, and then was purified by using a resin column in the same way as in method A above to give 506 mg. of 7-{D-(−)-α-[2-hydroxy-6-(p-tolyl)pyridine-3-carbonylamino]-p-hydroxyphenylacetamido}-3-(1-methyl-1,2,3,4-tetrazole-5-ylthiomethyl)-3-cephem-4-carboxylic acid.

EXAMPLE 57

Method A

In 4 ml. of water was supended 200 mg. of 7-{D-(−)-α-[2-hydroxy-6-(p-tolyl)pyridine-3-carbonylamino]-phenylacetamido}-3-acetoxymethyl-3-cephem-4-carboxylic acid, and 83 mg. of sodium bicarbonate was added thereto and dissolved. To the mixture was added 53 mg. of 5-mercapto-1-methyl-1,2,3,4-tetrazole, and the resulting mixture was heated at 65° C. for 8 hours. Thereafter the mixture was passed through a column packed with resin HP-50 to give 32 mg. of sodium salt of 7-{D-(−)-α-[2-hydroxy-6-(p-tolyl)pyridine-3-carbonylamino]-phenylacetamido}-3-(1-methyl-1,2,3,4-tetrazole-5-ylthiomethyl)-3-cephem-4-carboxylic acid melting at 185° to 190° C. (decomp.).

NMR spectrum (DMSO-d$_6$-TMS) δ(ppm): 2.30 (3H, s, tolyl—C$\underline{H}_3$); 3.50 (2H, ABq., —C$\underline{H}_2$— at 2-position); 3.95 (3H, s, N—C$\underline{H}_3$); 4.30 (2H, ABq., —C$\underline{H}_2$— at 3-position); 4.90 (1H, d, J=5.0 Hz, H at 6-position); 5.60 (1H, dd, H at 7-position); 5.90 (1H, d, J=7 Hz,

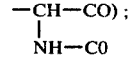

6.80 (1H, d, J=8 Hz, proton at pyridine ring); 7.35 (7H, m, proton at phenyl ring and at p-hydroxyphenyl ring); 8.30 (1H, d, proton at pyridine ring); 9.30 (1H, d, J=7 Hz,

11.10 (1H, d, J=7 Hz,

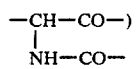

IR spectrum (Nujol) cm$^{-1}$: 1760 (β-lactam), 1660 (CONH), 1610 (COO$^\ominus$).

Method B

In 8 ml. of anhydrous methylene chloride and anhydrous dimethylformamide was dissolved 1.3 g. of 7-{D-(−)-α-aminophenylacetamido}-3-(1-methyl-1,2,3,4-tetrazole-5-ylthiomethyl)-3-cephem-4-carboxylic acid, and 0.8 ml. of triethylamine and 800 mg. of p-nitrophenyl ester of 2-hydroxy-6-(p-tolyl)pyridine-3-carboxylic acid were added thereto, and then the resulting mixture was subjected to reaction at room temperature for 18 hours. Insoluble substances were removed by filtration and the filtrate was concentrated to dryness, and to the thus obtained syrup was added 10 ml. of 1 N-HCl to precipitate crystals. Further, after filtration and washing with water and ether, the crystals were converted to sodium salt of the desired product by adding sodium bicarbonate and dimethylformamide thereto. Then the crystals were purified by using a resin column in the same manner as in method A above to give 350 mg. of sodium salt of 7-{D-(−)-α-[2-hydroxy-6-(p-tolyl)pyridine-3-carbonylamino]-phenylacetamido}-3-(1-methyl-1,2,3,4-tetrazole-5-ylthiomethyl)-3-cephem-4-carboxylic acid.

What is claimed is:

1. A cephalosporin compound of the formula

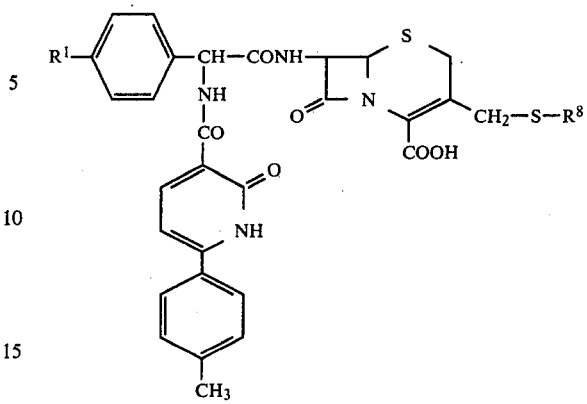

wherein $R^1$ represents a hydrogen atom or a hydroxy group, and $R^8$ represents a 5-carbamoyl-1,3,4-thiadiazol-2-yl or 1-methyl-1,2,3,4-tetrazol-5-yl group and pharmaceutically acceptable salts thereof.

2. A cephalosporin compound and a pharmaceutically acceptable salt thereof as claimed in claim 1 wherein the compound is 7-{D(−)-α-[2-hydroxy-6-(p-tolyl)pyridine-3-carbonylamino]phenylacetamido}-3-(5-carbamoyl-1,3,4-thiadiazol-2-ylthiomethyl)-3-cephem-4-carboxylic acid.

3. A cephalosporin compound and a pharmaceutically acceptable salt thereof as claimed in claim 1 wherein the compound is 7-{D(−)-α-[2-hydroxy-6-(p-tolyl)pyridine-3-carbonylamino]-p-hydroxyphenylacetamido}-3-(5-carbamoyl-1,3,4-thiadiazol-2-ylthiomethyl)-3-cephem-4-carboxylic acid.

4. A cephalosporin compound and a pharmaceutically acceptable salt thereof as claimed in claim 1 wherein the compound is 7-{D(−)-α-[2-hydroxy-6-(p-tolyl)pyridine-3-carbonylamino]-p-hydroxyphenylacetamido}-3-(1-methyl-1,2,3,4-tetrazol-5-ylthiomethyl)-3-cephem-4-carboxylic acid.

5. A cephalosporin compound and a pharmaceutically acceptable salt thereof as claimed in claim 1 wherein the compound is 7-{D(−)-α[2-hydroxy-6-(p-tolyl)pyridine-3-carbonylamino]phenylacetamido}-3-(1-methyl-1,2,3,4-tetrazol-5-ylthiomethyl)-3-cephem-4-carboxylic acid.

* * * * *

UNITED STATES PATENT AND TRADEMARK OFFICE
CERTIFICATE OF CORRECTION

PATENT NO. : 4,258,184
DATED : March 24, 1981
INVENTOR(S) : FUMIO KAI et al

It is certified that error appears in the above—identified patent and that said Letters Patent is hereby corrected as shown below:

Title page, left column, under the heading "FOREIGN APPLICATION PRIORITY DATA", delete "Mar. 13, 1978 [JP] Japan ..........53/27784".

Column 1, line 18, insert --Formula (V):--.

Signed and Sealed this

Fifteenth Day of June 1982

[SEAL]

Attest:

GERALD J. MOSSINGHOFF

Attesting Officer

Commissioner of Patents and Trademarks